(12) United States Patent
Yanai et al.

(10) Patent No.: US 9,296,225 B2
(45) Date of Patent: Mar. 29, 2016

(54) INFORMATION PROCESSING APPARATUS, INFORMATION PROCESSING METHOD, IMAGE FORMING APPARATUS, AND STORAGE MEDIUM

(71) Applicant: CANON KABUSHIKI KAISHA, Tokyo (JP)

(72) Inventors: Tomokazu Yanai, Kawasaki (JP); Ryosuke Otani, Tokyo (JP); Yoshinori Shindo, Kawasaki (JP); Masashi Oya, Soka (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/561,708

(22) Filed: Dec. 5, 2014

(65) Prior Publication Data

US 2015/0168134 A1 Jun. 18, 2015

(30) Foreign Application Priority Data

Dec. 17, 2013 (JP) ................................ 2013-260508

(51) Int. Cl.
*B41J 29/38* (2006.01)
*B41J 11/00* (2006.01)
*G01N 21/00* (2006.01)

(52) U.S. Cl.
CPC ............... *B41J 11/009* (2013.01); *G01N 21/00* (2013.01)

(58) Field of Classification Search
USPC ................... 347/14, 16, 19, 43, 105; 382/108
See application file for complete search history.

(56) References Cited

U.S. PATENT DOCUMENTS

2004/0008869 A1* 1/2004 Tsujimoto .................... 382/108

FOREIGN PATENT DOCUMENTS

JP 2001-88275 4/2001

* cited by examiner

*Primary Examiner* — Lam Nguyen
(74) *Attorney, Agent, or Firm* — Fitzpatrick, Cella, Harper & Scinto

(57) ABSTRACT

Conventionally, it has not been possible to perform detailed printing control in accordance with a purpose, such as the improvement in density and the improvement in rubfastness, by taking into consideration a slight difference in the kind of paper (slight difference in the receptive layer), such as matte paper and glossy paper. An information processing apparatus for determining a printing medium having a receptive layer has a transmitted light information acquisition unit configured to acquire information on transmitted light by irradiating a printing medium on which a determination image is printed with light, and a surface characteristics determination unit configured to determine the surface characteristics of the printing medium on which the determination image is printed based on the information on transmitted light.

15 Claims, 27 Drawing Sheets

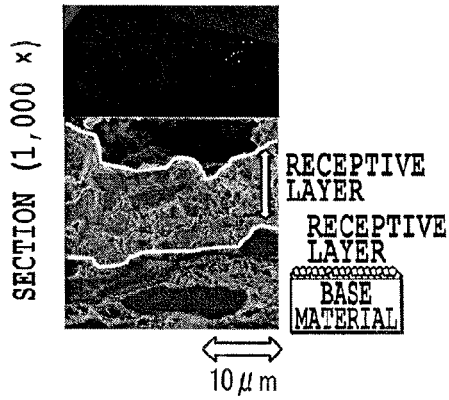
FIG.1A
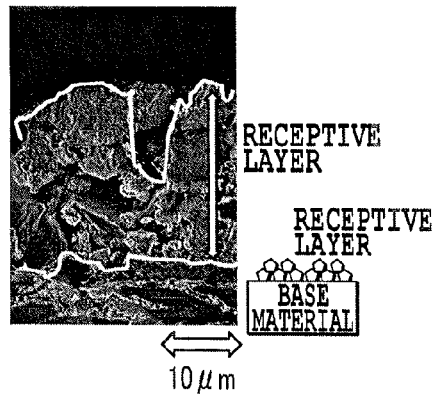
FIG.1B
| THICKNESS OF RECEPTIVE LAYER | THIN, ABOUT 10 μm | THICK, ABOUT 20μm |
|---|---|---|
| RECEPTIVE LAYER PARTICLE DIAMETER | SMALL, 3 TO 5μm | LARGE, 5 TO 20μm |
| DEPOSITION DENSITY OF RECEPTIVE LAYER | HIGH | LOW |
FIG.1C

DEPOSITION DENSITY IS LOW

DEPOSITION DENSITY IS HIGH

100[μm]

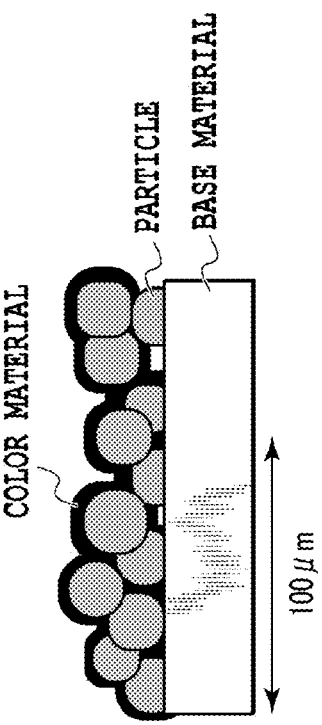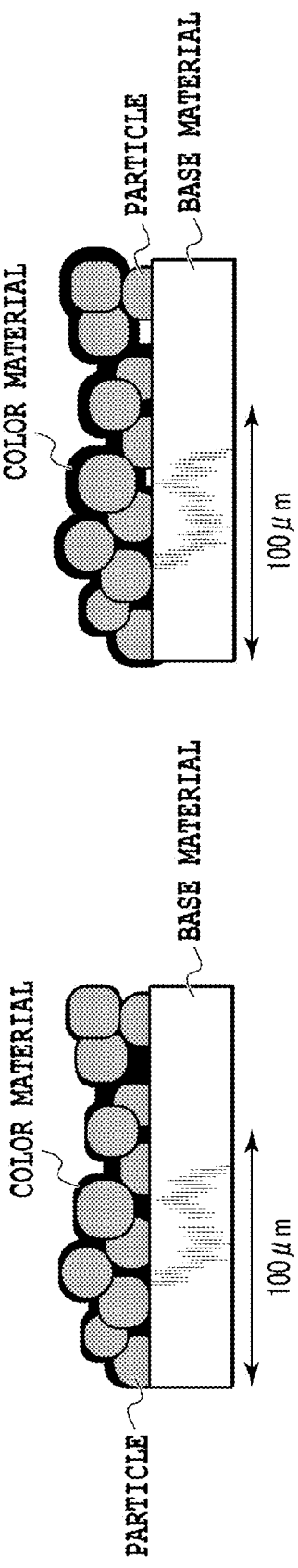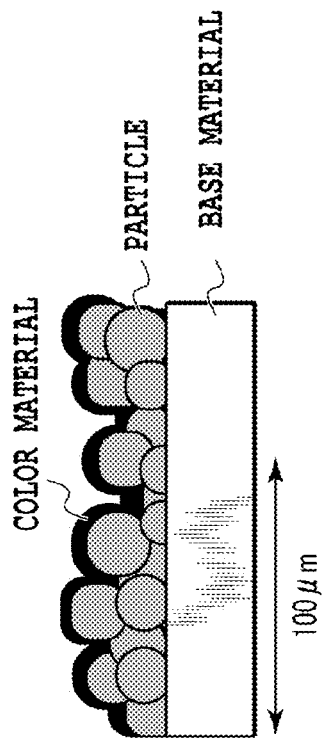

PARTICLE DIAMETER IS SMALL

PARTICLE DIAMETER IS LARGE

↔ 100[μm]

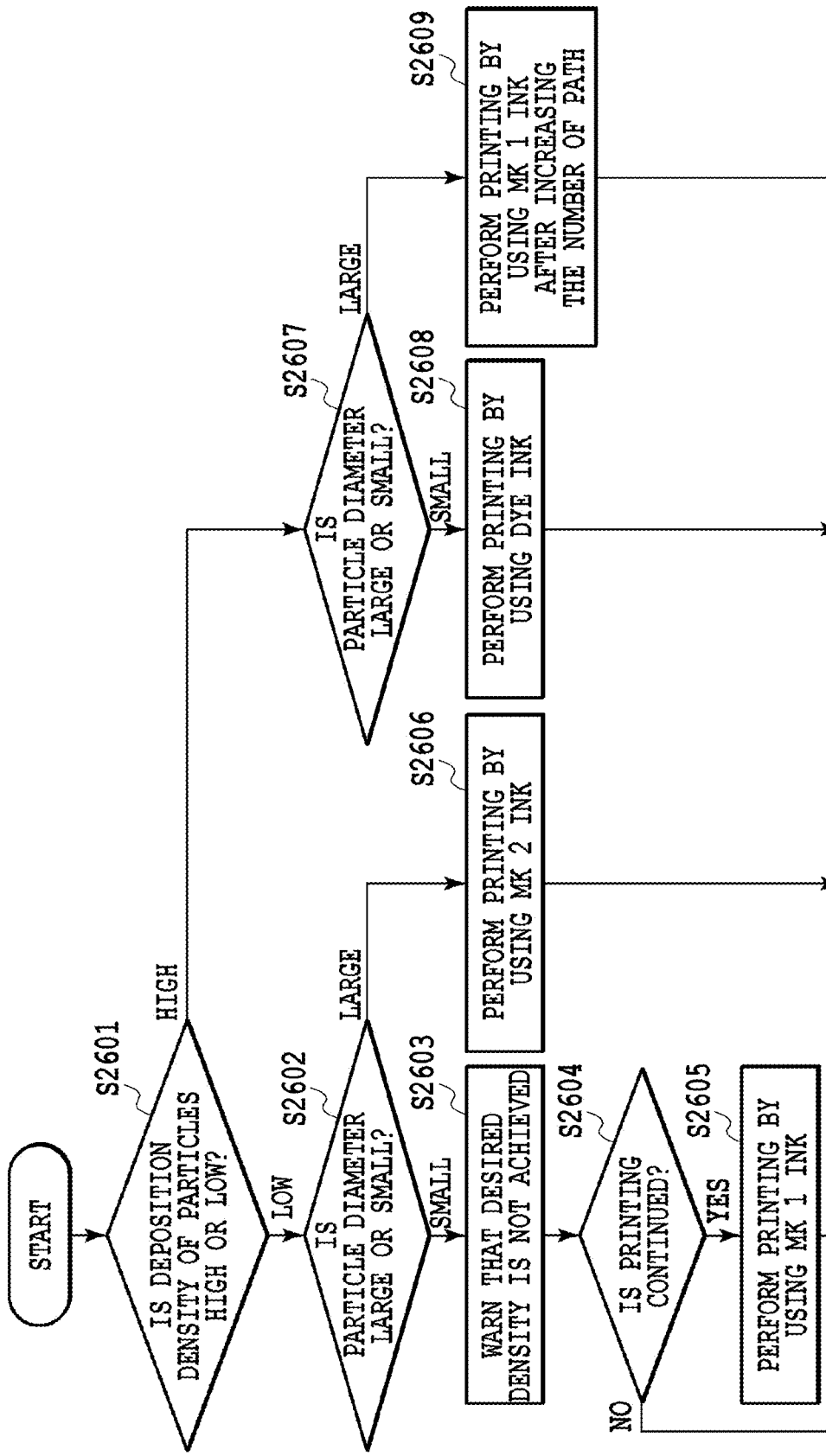

INFORMATION PROCESSING APPARATUS, INFORMATION PROCESSING METHOD, IMAGE FORMING APPARATUS, AND STORAGE MEDIUM

BACKGROUND OF THE INVENTION

1. Field of the Invention

The present invention relates to a technique for determining a printing medium based on the surface characteristics of the printing medium.

2. Description of the Related Art

There are a variety of types of recording apparatuses for recording information, such as characters and images, on a printing medium in the form of a sheet, such as paper and a film. Among them, a type for forming text or an image on a printing medium by attaching a recording agent (color material) to the printing medium has been put to practical use. As a representative example of such a type, an inkjet recording apparatus using a recording head including a plurality of ink ejection outlets is known. Photoprinting by an inkjet recording apparatus has spread widely and a dye ink using dye that is easily dissolved in water has been widely applied to the photoprinting. However, because of the demand for the improvement in light resistance and water resistance of printed matter in recent years, the utilization of a pigment ink has been promoted. The pigment ink exists in a solvent as particles in size from tens of nanometers to several micrometers, unlike dye that exists as molecules. As described above, the particle of the pigment ink is large compared to that of the dye ink, and therefore, it is known that printed matter with a high light resistance and a high water resistance can be obtained.

As described above, the pigment ink is superior to the dye ink in the light resistance and water resistance, but there has been such a problem that the color development properties change depending on the surface characteristics of the receptive layer in a printing medium. While the dye ink dyes the particles constituting the receptive layer in a printing medium by permeating into the inside thereof, the pigment ink dyes the particles constituting the receptive layer by depositing on the surface thereof. Because of this, in the case where an image is formed on a printing medium on which small holes or cracks larger in size than the color material particle included in the pigment ink exist, the color material flows into the inside of the printing medium and the color material distribution becomes ununiform, and therefore, the color development properties are degraded.

On the other hand, in order to implement the color tone and texture supposed by a user, a plurality of kinds of printing media having different surface characteristics has begun to be used. For example, such printing media include glossy paper whose receptive layer particle diameter is on the order of nm, matte paper whose receptive layer particle diameter is about 3 μm or more, plain paper having no receptive layer, etc. In the case where printing is performed by using the pigment ink as described above, it is necessary for a user to appropriately change the printing conditions in accordance with the surface characteristics of the printing medium that the user uses, but it is very troublesome for the user to change the printing conditions each time the kind of printing medium is changed.

Because of this, conventionally, a method for automatically determining the kind of printing medium to change printing conditions in accordance with the determination results has been proposed. A method for reading a barcode or symbol formed on a printing medium in advance and a method for determining the surface asperity and ink permeability of a printing medium based on the amount of light reflected from the surface of the printing medium on which color material is placed to change printing conditions (Japanese Patent Laid-Open No. 2001-088275) are known.

Even by the conventional technique, it is possible to determine the kind of a printing medium that a user is going to use among plain paper, glossy paper, and matte paper. However, various kinds of recording media are used for forming an image. For example, in the case of so-called coated paper, such as matte paper and glossy paper, in general, a receptive layer mainly including silica or aluminum on the base material is provided, but the structure thereof differs depending on the kind of paper, such as matte paper and glossy paper. For example, the receptive layer particle diameter of the matte paper is about 3 μm when it is small, but the diameter may be about 20 μm when it is large. Further, a deposition density representing a ratio of the volume of particles included within the receptive layer to the volume of air included therein is about 35% when the deposition density is low, but the deposition density may be about 75% when it is high. FIGS. 1A and 1B are section photos of the form of the surface of matte paper and FIG. 1A shows matte paper of the kind whose receptive layer particle diameter is as small as 3 to 5 μm and whose particle deposition density is high, and FIG. 1B shows matte paper of the kind whose receptive layer particle diameter is as large as 5 to 20 μm and whose particle deposition density is low. FIG. 1C is a table summarizing the relationship between the thickness of the receptive layer, the particle diameter, and the deposition density.

As described above, there are a variety of kinds of matte paper and the small holes and cracks on the paper surface are different depending on the receptive layer particle diameter and the deposition density. Then, there has been such a problem that the density and rubfastness are affected because a ratio of the amount of color material that deposits on the paper surface to the amount of color material that flows into the inside of the receptive layer changes depending on the relationship in size between the small holes and cracks, and the color material particles included in the pigment ink.

With regard to this point, by the conventional technique, it is possible to determine a difference between the glossy paper whose receptive layer particle diameter is on the order of nm and the matte paper whose receptive layer particle diameter is on the order of μm, but it has been difficult to determine a slight difference between the kinds of matter paper and glossy paper. Because of this, it has not been possible to perform detailed printing control in accordance with a purpose, such as the improvement in density and the improvement in rubfastness, by taking into consideration the slight difference between the kinds of matter paper and glossy paper.

SUMMARY OF THE INVENTION

An information processing apparatus according to the present invention is an information processing apparatus for determining a printing medium having a receptive layer and includes a transmitted light information acquisition unit configured to acquire information on transmitted light by irradiating a printing medium on which an image for determination is printed with light, and a surface characteristics determination unit configured to determine the surface characteristics of the printing medium on which the image for determination is printed based on the information on transmitted light.

According to the present invention, it is possible to easily determine a difference between types (surface characteristics) of coated paper.

Further features of the present invention will become apparent from the following description of exemplary embodiments (with reference to the attached drawings).

BRIEF DESCRIPTION OF THE DRAWINGS

FIGS. 1A and 1B are section photos of a surface shape of matte paper, and FIG. 1C is a table summarizing the relationship between the thickness of the receptive layer, the particle diameter, and the deposition density;

FIGS. 15A to 15C are schematic diagrams showing how ink fixes onto the printing medium as the results of performing the printing processing;

FIG. 19A is a general diagram, FIG. 19B is a schematic section diagram from the front, and FIG. 19C is a schematic section diagram from the side;

FIG. 23A shows the case where the receptive layer particle diameter is small, and FIG. 23B shows the case where the receptive layer particle diameter is large;

FIG. 26 is a flowchart showing a flow of specific processing in printing control processing according to the third embodiment.

DESCRIPTION OF THE EMBODIMENTS

In each embodiment below, the case where a printing medium is matte paper is explained mainly as an example, but the present invention is not limited to matte paper and the present invention can be applied widely to general coated paper having a receptive layer. Hereinafter, embodiments for embodying the present invention are explained in detail by using the drawings.

First Embodiment

Figure 2:
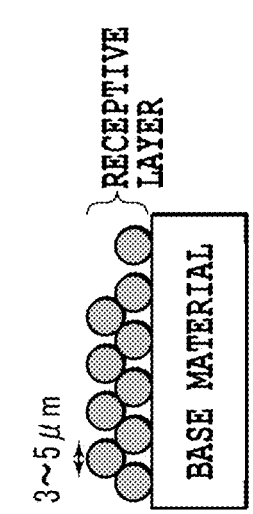
FIG. 2 is a table indicating schematic diagrams of matte paper according to type, which is provided with a receptive layer mainly including silica on a base material.

FIG. 2 is a table indicating schematic diagrams of matte paper according to type, which is provided with a receptive layer mainly containing silica on a base material. In FIG. 2, (a) is a schematic diagram of matte paper whose receptive layer particle diameter is as small as 3 to 5 μm, whose deposition density is low, and whose thickness of the receptive layer is about 10 μm. In FIG. 2, (b) is a schematic diagram of matte paper whose receptive layer particle diameter is as small as 3 to 5 μm, whose deposition density is high, and whose thickness of the receptive layer is about 10 μm. In FIG. 2, (c) is a schematic diagram of matte paper whose receptive layer particle diameter is as large as 5 to 20 μm, whose deposition density is low, and whose thickness of the receptive layer is about 20 μm. In FIG. 2, (d) is a schematic diagram of matte paper whose receptive layer particle diameter is as large as 5 to 20 μm, whose deposition density is high, and whose thickness of the receptive layer is about 20 μm.

In the present embodiment, based on the premise that the above-mentioned four kinds of matte paper exist, an aspect is explained in which the kind of matte paper is determined by estimating the deposition density of particles constituting the receptive layer and appropriate printing control in accordance with a purpose, such as the improvement in density and the improvement in rubfastness is performed. It is assumed that the deposition density means a void ratio indicating a ratio between the volume of air included within the receptive layer and the volume of particles. However, the index indicating the deposition density may be an index based on the ratio of weights and measures, such as, for example, g/cc and kg/m$^2$, in addition to % notation.

Figure 3:
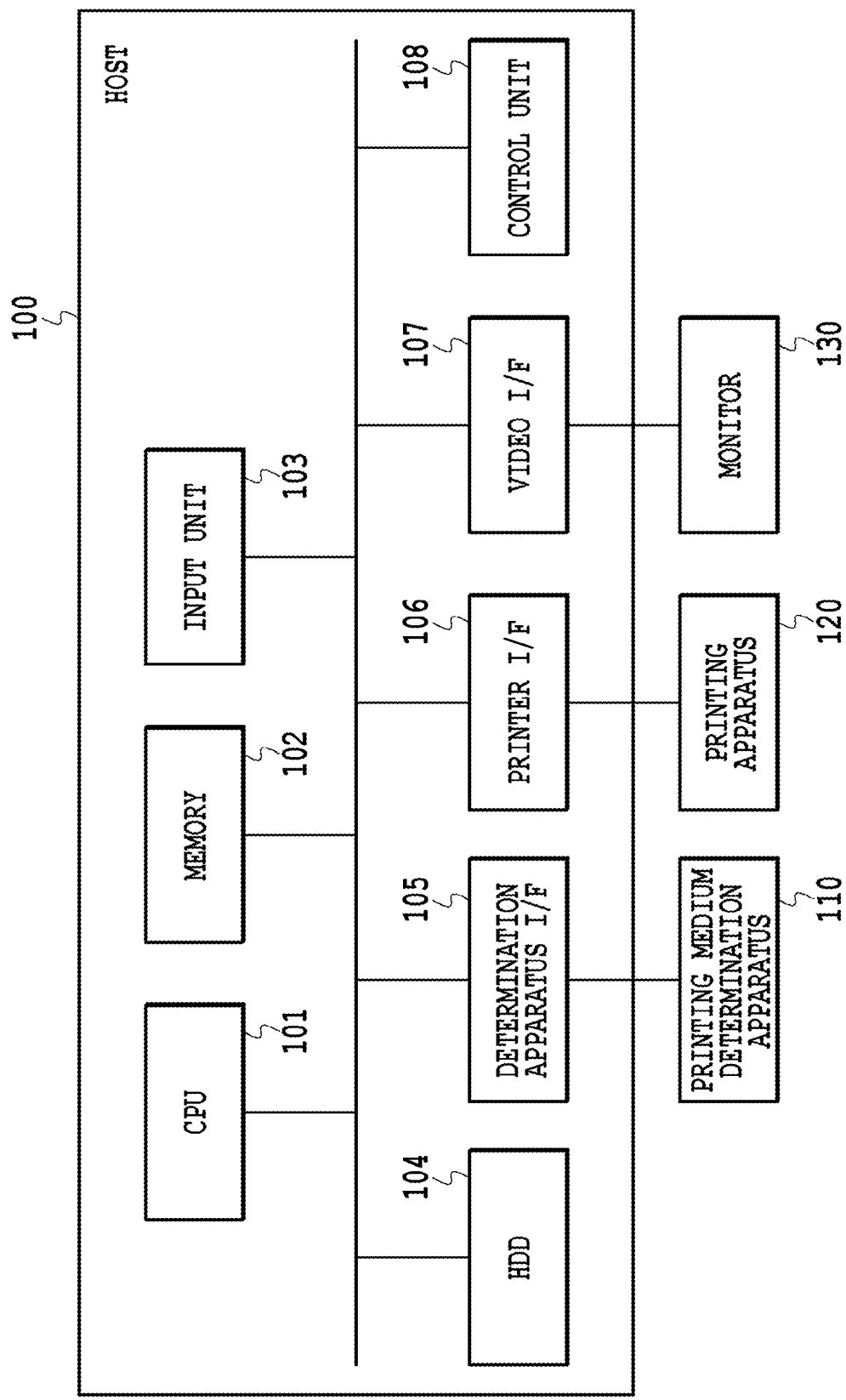
FIG. 3 is a diagram showing an example of a configuration of a printing system according to a first embodiment.

FIG. 3 is a diagram showing an example of a configuration of a printing system according to the present embodiment.

In FIG. 3, a host 100 as an information processing apparatus is, for example, a computer and includes a CPU 101, a memory 102, an input unit 103, such as a keyboard, and an HDD 104 as a storage device. Besides, the host 100 includes a communication interface (determination apparatus I/F) 105 with a printing medium determination apparatus 110, a communication interface (printer I/F) 106 with a printing apparatus 120, and a communication interface (video I/F) 107 with a monitor 130. Further, the host 100 includes a control unit 108 configured to perform control for printing based on the results of determination of a printing medium type in the printing medium determination apparatus 110, to be described later.

The CPU 101 performs various kinds of processing in accordance with programs stored in the memory 102 and in particular, performs various kinds of processing, such as conversion into multivalued data, resolution conversion, color matching, color conversion, halftoning, and multipath division, which relate to the present embodiment. These programs are stored in the HDD 104 or are supplied from an externally connected device, not shown. The multipath refers to a printing method for completing an image by causing a recording head to scan a predetermined recording range a plurality of times and the number of times of the recording scan required to complete an image is called a path number. The host 100 receives various kinds of information through the input unit 103 as well as outputting various kinds of information to the monitor 130 via the video I/F 107. Further, the host 100 is connected to the printing medium determination apparatus 110 via the determination apparatus I/F 105 and receives information indicative of the results of determination of a printing medium, which are the processing results, from the printing medium determination apparatus 110 as well as transmitting data to cause the printing medium determination apparatus 110 to perform the processing to determine a printing medium. Furthermore, the host 100 is connected to the printing apparatus 120 via the printer I/F 106 and receives information about the completion of printing, the shortage of ink, etc., from the printing apparatus 120 as well as transmitting data to the printing apparatus 120 to cause the printing apparatus 120 to form an image.

In the present embodiment, the communication interfaces for the printing apparatus 120 and the printing medium determination apparatus 110 are provided separately, but it may also be possible to, for example, connect the two apparatuses by one communication interface.

Further, in the present embodiment, the printing system is such that the printing medium determination apparatus 110 and the printing apparatus 120 are connected via the host 100, but the printing system may be a single printing apparatus (image forming apparatus) that incorporates the function of the host 100 and the function of the printing medium determination apparatus 110.

In the following, explanation is given on the assumption that the method at the time of forming an image on a printing medium is the multipath method in which a recording head is caused to perform a scan a plurality of times, but the single path method that uses, for example, a long recording head may be used.

<Outline of Configuration of Printing Apparatus 120>

Figure 4:
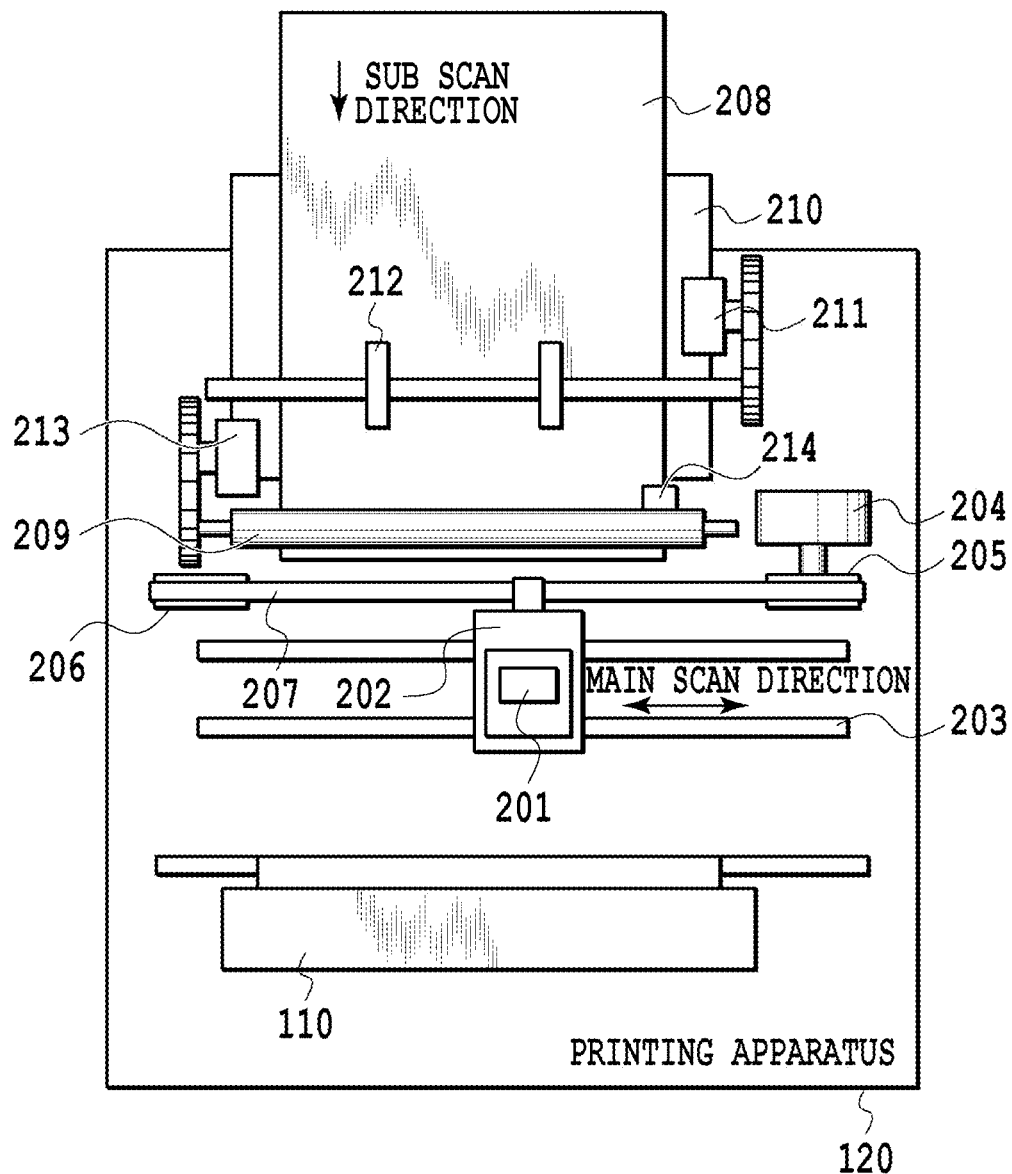
FIG. 4 is a diagram showing an internal configuration of a printing apparatus according to the first embodiment.

FIG. 4 is a diagram showing an internal configuration of the printing apparatus 120 according to the present embodiment.

The printing apparatus 120 is an inkjet printer that forms an image on a printing medium 208 using ink and incorporates the printing medium determination apparatus 110 inside thereof and includes a function to determine the surface characteristics of the printing medium 208. As described above, the printing medium 208 here is matte paper provided with the receptive layer mainly containing silica whose particle diameter is about 3 to 20 μm on the surface of the base material.

A head cartridge 201 includes a recording head including a plurality of ejection outlets and tanks of inks in a plurality of colors that supply the inks to the recording head. It is assumed that the head cartridge 201 has seven ink colors: sK (dye black), C (cyan), M (magenta), Y (yellow), PK (photo black), MK1 (matte black 1), and MK2 (matte black 2). The color sK is the color of the dye ink and the other colors are the colors of the pigment ink. PK is the color of the pigment ink having a small amount of pigment and a small particle diameter and highly suitable mainly to glossy paper. MK1 (matte black 1) is the color of the pigment ink having a standard viscosity and MK2 (matte black 2) is the color of the pigment ink having a relatively high viscosity. In the following, these inks are referred to as color material as a generic term. The head cartridge 201 is provided with a connector for transmitting and receiving a signal etc. to drive each ejection outlet of the recording head. The head cartridge 201 is aligned with a carriage 202 and mounted thereon in a replaceable manner, and the carriage 202 is provided with a connector holder for transmitting a drive signal etc. to the head cartridge 201 via the connector.

Reference numeral 203 represents a guide shaft. The carriage 202 is enabled to reciprocate along the guide shaft 203. Specifically, the carriage 202 is driven via drive mechanisms, such as a motor pulley 205, a driven pulley 206, and a timing belt 207, by using a main scanning motor 204 as a drive source and at the same time, the position and the movement of the carriage 202 are controlled. The printing medium 208 is mounted on an auto sheet feeder (hereinafter, called an "ASF") 210 and is separated and fed one by one from the ASF 210 at the time of printing by rotating a pickup roller 212 by the drive of a feeder motor 211 via a gear. Further, the printing medium 208 is conveyed to a recording start position in opposition to the ejection outlet surface of the head cartridge 201 on the carriage 202 by the rotation of a conveyance roller 209. The conveyance roller 209 is driven via a gear by using a line feeder (hereinafter, called an "LF") motor 213 as a drive source. Determination of whether the printing medium 208 has been fed and settlement of the cue position at the time of feeding are performed at the point of time of the printing medium 208 passing by a paper end sensor 214. The head cartridge 201 mounted on the carriage 201 is held so that the ejection outlet surface protrudes downward from the carriage 202 and becomes parallel to the printing medium 208.

Figure 5B:
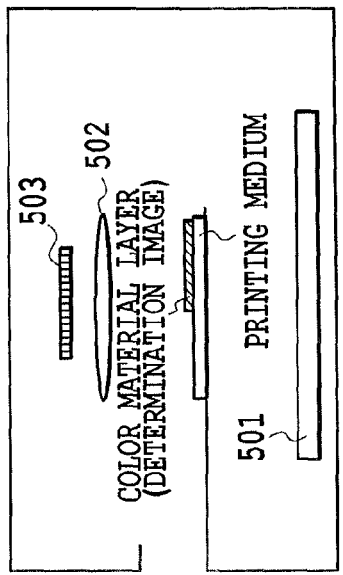
FIG. 5B is a schematic section diagram from the front.
Figure 5C:
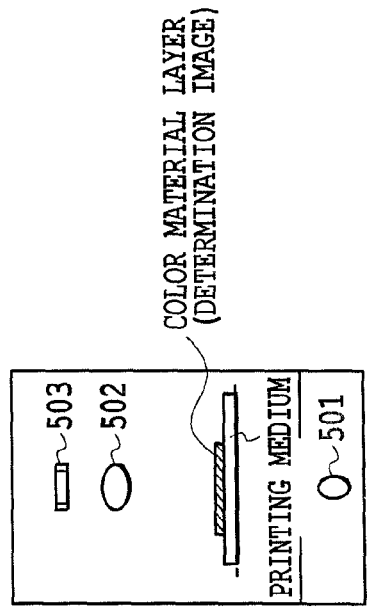
FIG. 5C is a schematic section diagram from the side.
Figure 5A:
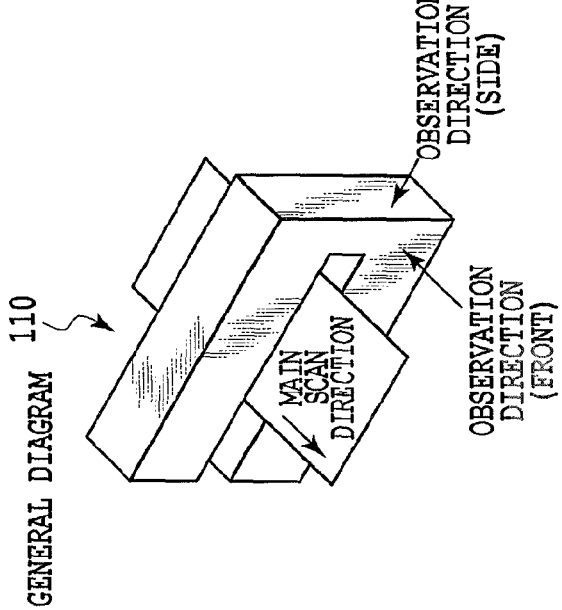
FIG. 5A is a general diagram of a printing medium determination apparatus according to the first embodiment.

The printing medium determination apparatus 110 is arranged downstream in the sub scan direction of the printing apparatus 120. FIGS. 5A to 5C are diagrams explaining an outline of the printing medium determination apparatus 110 according to the present embodiment: FIG. 5A is a general diagram thereof, FIG. 5B is a schematic section diagram from the front, and FIG. 5C is a schematic section diagram from the side. As shown in FIG. 5A, the printing medium determination apparatus 110 is in the shape of a reversed C so as to sandwich the printing medium 208 that has been conveyed. Further, as shown in FIGS. 5B and 5C, the printing medium 208 is illuminated from the backside by a white fluorescent lamp 501 having power in the entire visible light wavelength range. Transmitted light, which is part of the illumination light from the white fluorescent lamp 501, having passed through the printing medium 208 and a color material layer and traveling in the direction normal thereto is condensed by a condensing lens 502 arranged on the surface side of the printing medium 208. The color material layer referred to here is a layer formed by the color material that has fixed to the inside and/or the surface of the receptive layer of the printing medium 208 by the application of the color material, and means a region in which an image (hereinafter, called a "determination image") for determining the kind of the printing medium 208 is printed. The light path length of the condensed light is adjusted by a mirror lens, not shown, and converted into a light amount at each position by a line sensor 503. After the light amount at each position in the main scan direction of the printing medium 208 is detected, the printing medium 208 is conveyed by the rotation of the conveyance roller 209 and light amount detection at the next position is performed. A desirable configuration is such that the light amount detection and the conveyance such as the above are repeated and preferably a light amount is detected in units of 4,800 dpi both in the main scan and in the sub scan.

The device that detects the transmitted light amount is not limited to the line sensor as described above. For example, it may also be possible to detect the transmitted light amount on the entire surface of the printing medium by the light source and the light receiving unit performing a scan like the recording head. Further, it may also be possible to adopt, for example, the CIS method that combines the SELFOC (registered trademark) lens and a light receiving element in place of the line sensor.

Figure 6:
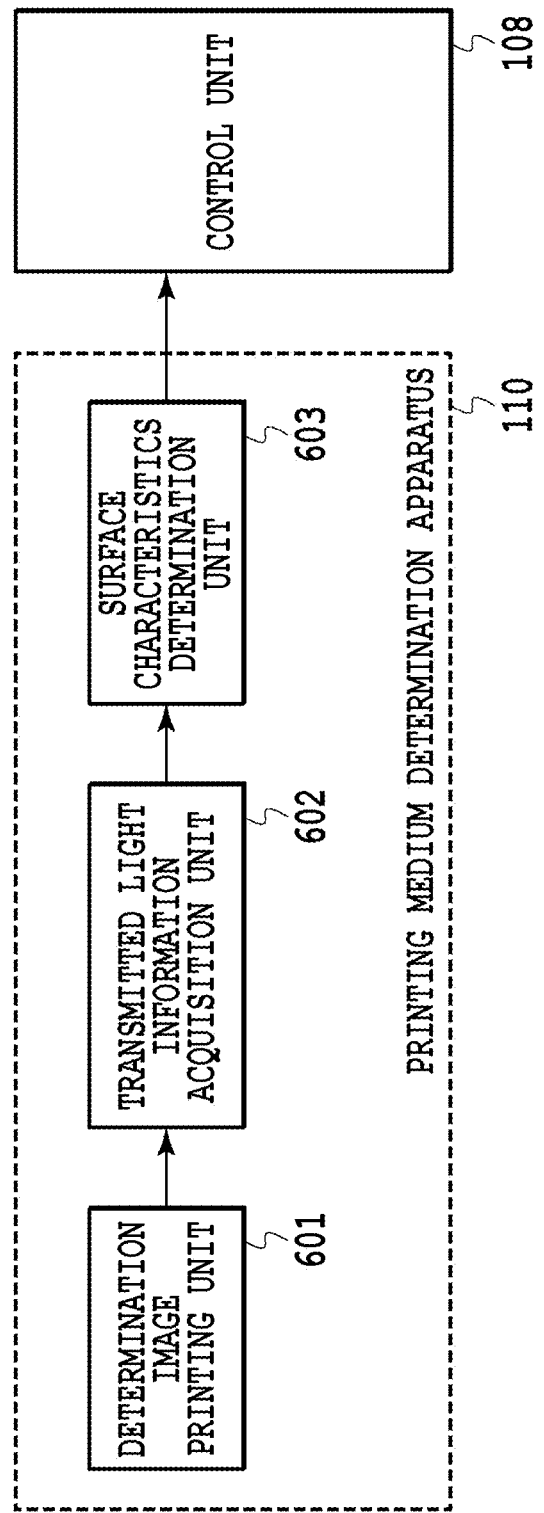
FIG. 6 is a block diagram showing a function configuration of the printing medium determination apparatus according to the first embodiment.

FIG. 6 is a block diagram showing a function configuration of the printing medium determination apparatus 110 according to the present embodiment. The printing medium determination apparatus 110 includes a determination image printing unit 601, a transmitted light information acquisition unit 602, and a surface characteristics determination unit 603. The final output (determination results) of the printing medium determination apparatus 110 is sent to the control unit 108 via the determination apparatus I/F 105.

<Flow of Processing in the Present Embodiment>

Figure 7:
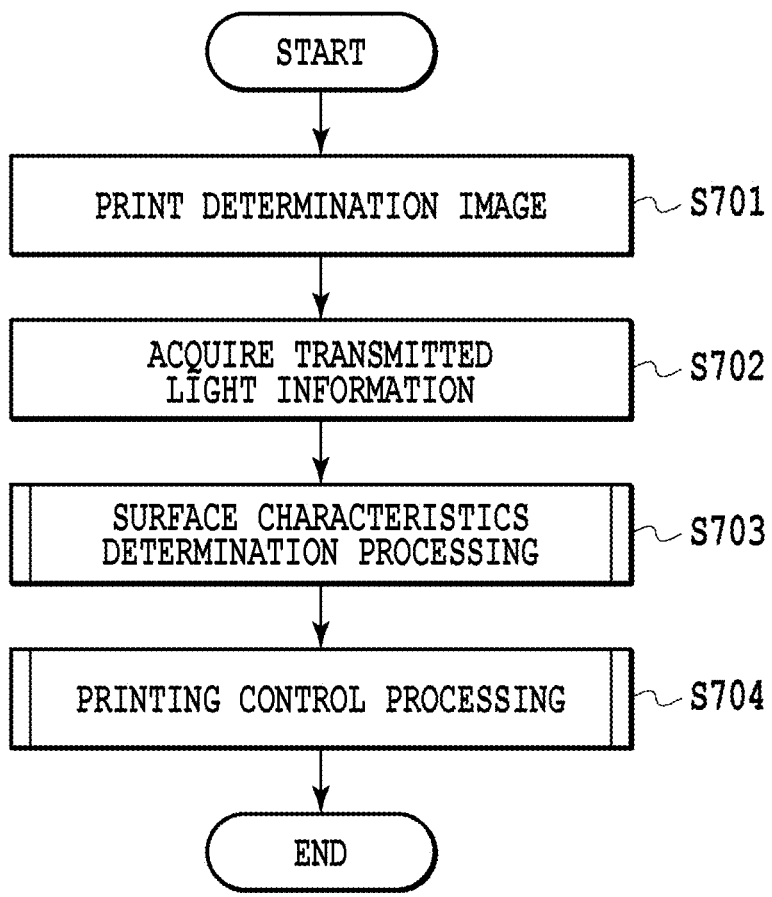
FIG. 7 is a flowchart showing a flow of each piece of the processing from printing of a printing medium determination image to printing control processing based on the determination results.

In the case where a request to perform processing to determine the kind of a printing medium is input by a user through the input unit 103, the input unit 103 notifies the CPU 101 of the start of determination processing. The CPU 101 having received the notification notifies the printing medium determination apparatus 110 of the start of the processing and performs each piece of the following processing. FIG. 7 is a flowchart showing a flow of each piece of the processing from printing of a determination image to printing control processing based on the determination results according to the present embodiment. The series of the processing is performed by the CPU 101 executing computer executable programs in which the procedures shown below are described after reading the programs from the HDD 104 onto the memory 102.

Figure 8:
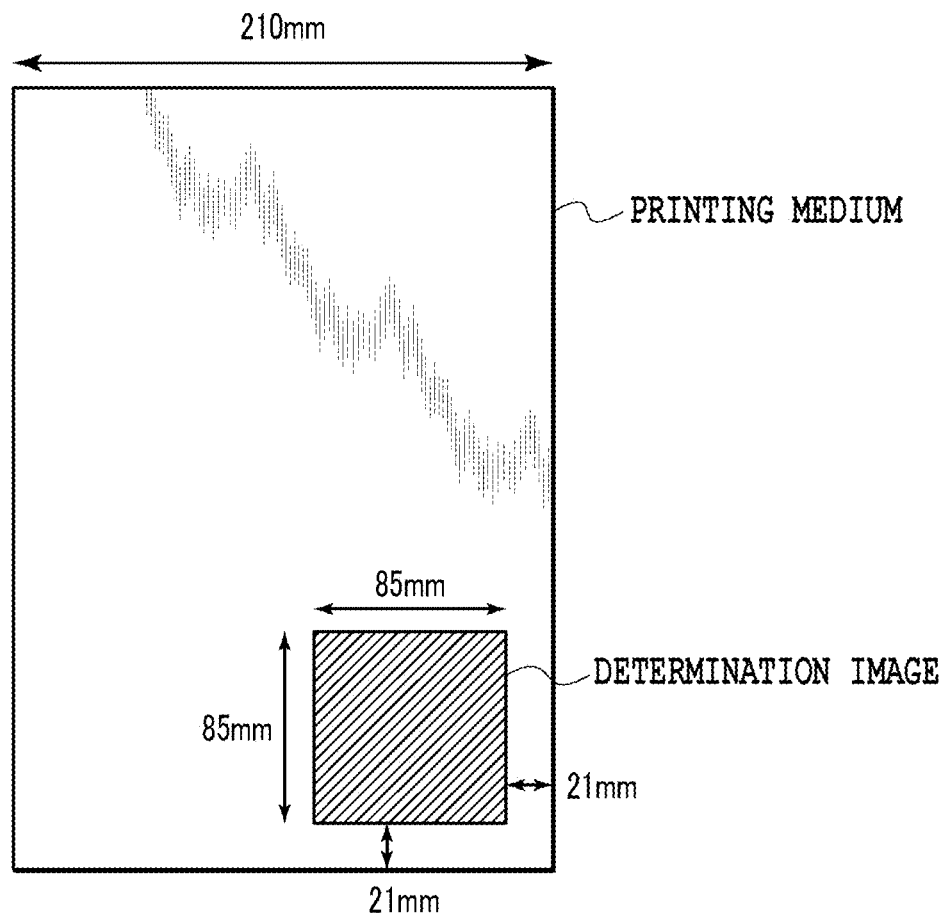
FIG. 8 is a diagram showing an example of a printing medium having an A4 size on which a determination image is printed.

At step 701, the CPU 101 gives instructions to print a determination image on a printing medium to the printing apparatus 120. Upon receipt of the instructions, the printing apparatus 120 prints the determination image at a predetermined position of the printing medium. In this case, the particle diameter of the color material used in printing of the determination image is large compared to the particle diameter of the particles (hereinafter, called "receptive layer particles") constituting the receptive layer of the printing medium. In other words, part of the region of the receptive layer is covered by using the color material whose particle diameter is larger than that of the receptive layer particle. FIG. 8 is a diagram showing an example of a printing medium having the A4 size on which the determination image is printed. A square determination image having a side of 85 mm is printed with a margin of 21 mm being provided both in the main scan direction and in the sub scan direction. The print position and the size of the determination image shown in FIG. 8 are an example and are not limited to this example. It is only required to be capable of identifying from which region the transmitted light comes mainly, which accounts for the light amount detected by the line sensor 503 in transmitted light information acquisition processing, which follows, by providing the region without a determination image (region in which the color material layer does not exist) and the region including a determination image (region in which the color material layer exists). For example, the determination image may have a size of 40 mm square and a margin of 40 mm, and the shape of the determination image may be a rectangle, not a square, or a shape other than a rectangle (e.g., circle). In the present embodiment, it is assumed that MK1 (matte black 1), which is the color of the color material whose particle diameter is large compared to that of sK and PK color material, is used in printing of the determination image because it is desired to know the density distribution characteristics of an image in the case where the color material having a standard ink viscosity is used. The printing medium on which the determination image is printed is conveyed up to the printing medium determination apparatus 110 and the printing apparatus 120 notifies the CPU 101 of the completion of conveyance.

At step 702, the CPU 101 gives instruction to acquire transmitted light information to the printing medium determination apparatus 110. Upon receipt of the instructions, the printing medium determination apparatus 110 causes the white fluorescent lamp 501 to emit light and acquires transmitted light information of the printing medium. Here, as the transmitted light information, information on the amount of light that has passed through the region in which the determination image is not printed in the entire region of the printing medium, and information on the amount of light that has passed through the region in which the determination image is printed (region in which the color material layer exists). After acquiring the transmitted light information, the printing medium determination apparatus 110 notifies the CPU 101 of the completion of the acquisition of transmitted light information.

At step 703, the CPU 101 gives instructions to perform processing to determine the surface characteristics of the printing medium to the printing medium determination apparatus 110. Upon receipt of the instructions, the printing medium determination apparatus 110 performs the processing ("surface characteristics determination processing") to determine the surface characteristics of the printing medium based on the transmitted light information acquired at step 702. After completing the determination of the surface characteristics, the printing medium determination apparatus 110 notifies the control unit 108 of the determination results.

At step 704, the control unit 108 performs the processing (printing control processing) to control printing in accordance with the kind of the printing medium (surface characteristics) based on the received determination results.

In the following, each process of the processing is explained in detail.

<About Printing of Determination Image>

After printing of the determination image is started at step 701, first, the printing medium is conveyed to a predetermined recording start position.

Next, the carriage 202 moves on the printing medium along the guide shaft 203 and during the movement, the MK1 (matte black 1) color material is ejected from the recording head ejection outlet of the ink cartridge 201. The movement of the carriage 202 along the guide shaft 203 is referred to as a "main scan" and the direction of the movement is referred to as a "main scan direction". Then, following the movement of the carriage 202 up to one end of the guide shaft 203, the conveyance roller 209 conveys the printing medium a predetermined amount of distance in the direction vertical to the scan direction of the carriage 202. This conveyance of the printing medium is referred to as "paper feed" or "sub scan" and the direction of the conveyance is referred to as a "paper feed direction" or "sub scan direction". After the conveyance of the printing medium by a predetermined amount of distance is completed, the carriage 202 moves again along the guide shaft 203. In this manner, the scan and the paper feed by the carriage 202 of the recording head are repeated, and thereby, the determination image is printed on the surface of the printing medium.

Figure 9:
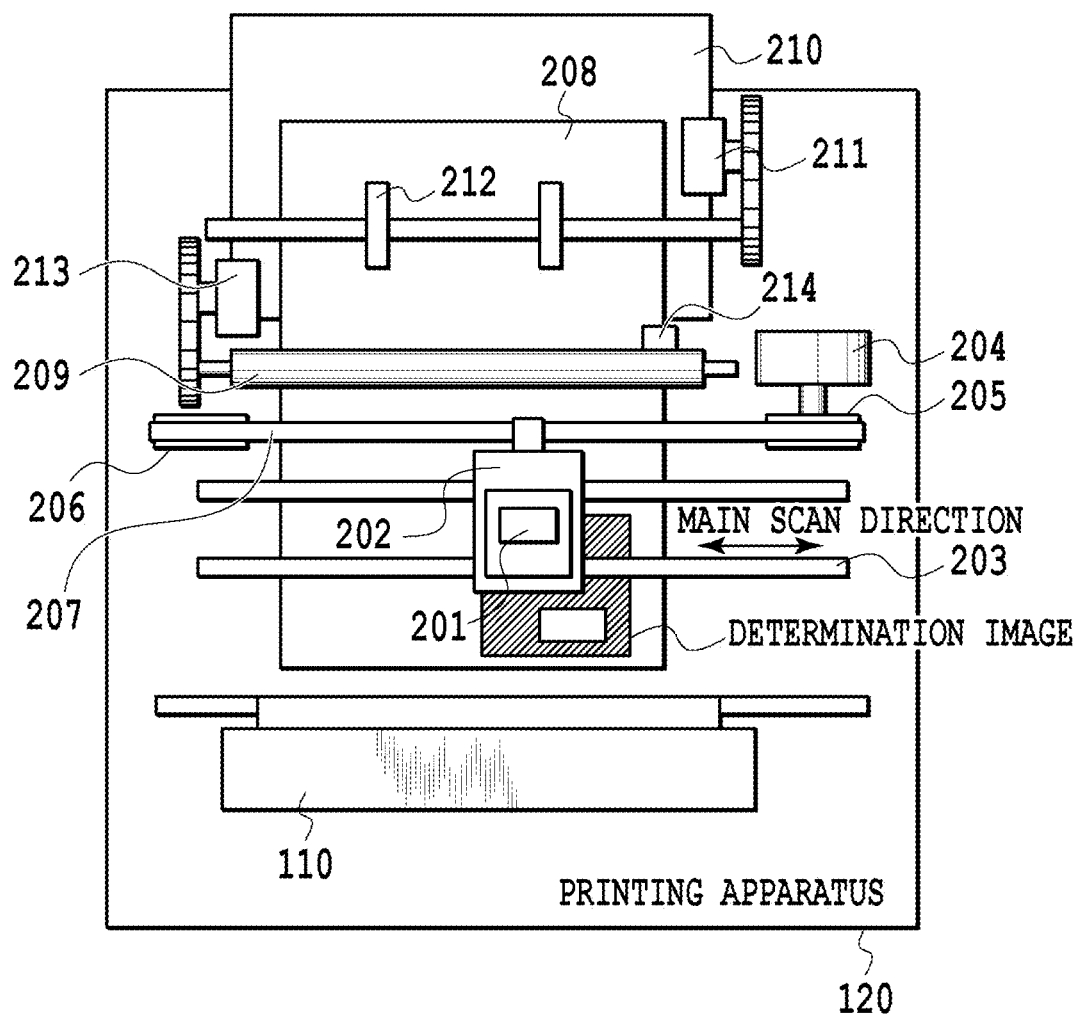
FIG. 9 is a diagram showing the way a printing medium on which a determination image is printed is conveyed to the printing medium determination apparatus.

The printing medium on which the determination image is printed (on which the color material layer is formed) is conveyed to the printing medium determination apparatus 110. FIG. 9 shows the way the printing medium 208 on which the determination image is printed is conveyed to the printing medium determination apparatus 110.

<About Acquisition of Transmitted Light Information>

Figure 10:
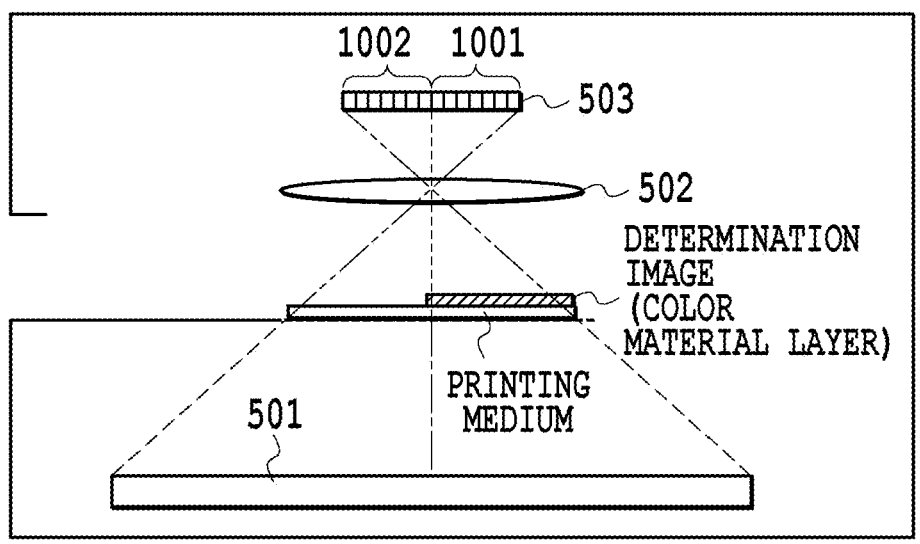
FIG. 10 is a diagram explaining how a transmitted light amount is obtained from a printing medium on which a determination image is printed.

As described above, in the processing to acquire transmitted light information at step 702, two kinds of information (transmitted light amount in the region in which the determination image is not printed and transmitted light amount in the region in which the determination image is printed) are acquired. FIG. 10 is a diagram explaining how the above-described two kinds of transmitted light amounts are obtained from the printing medium on which the determination image is printed. First, light irradiated from the white fluorescent lamp 501 and having passed through the printing medium is condensed by the condensing lens 502 and is received by the line sensor 503. Then, from the positional relationship between the pattern of the determination image and the line sensor 503, it is possible to obtain the above-described two kinds of transmitted light amounts, respectively. In detail, the amount of light detected by a right half 1001 of the line sensor 503 is taken to be a transmitted light amount Y trans_paper in the region in which the determination image is not printed, and the amount of light detected by a left half 1002 is taken to be a transmitted light amount Y trans_color in the region in which the determination image is printed, and thus, the above-described two kinds of transmitted light amounts are obtained. In the example shown in FIG. 10, the region in which the color material layer is formed and the region in which the color material layer is not formed are provided on the printing medium and the two kinds of transmitted light information are acquired at a time, but the example is not limited to this. For example, it may also be possible to measure Y trans_paper by conveying the printing medium up to the printing medium determination apparatus 110 before printing the determination image on the printing medium and then, to measure Y trans_color after conveying the printing medium in the opposite direction, printing the determination image, and conveying the printing medium again in the main scan direction.

<About Surface Characteristics Determination Processing>

Figure 11A:
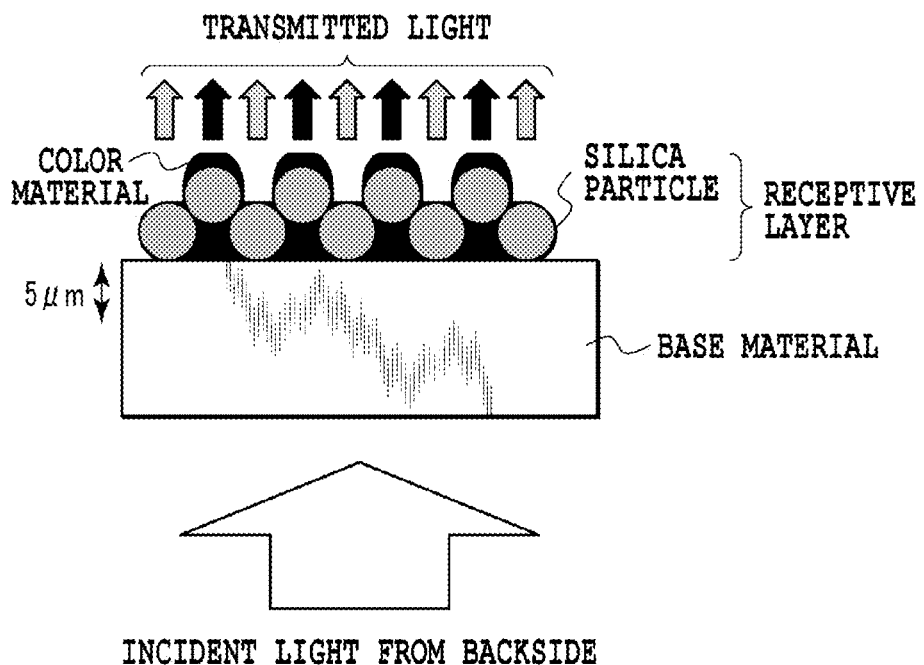
FIGS. 11A and 11B are diagrams explaining the way of thinking at the time of estimating a deposition density of receptive layer particles from a transmittance.
Figure 11B:
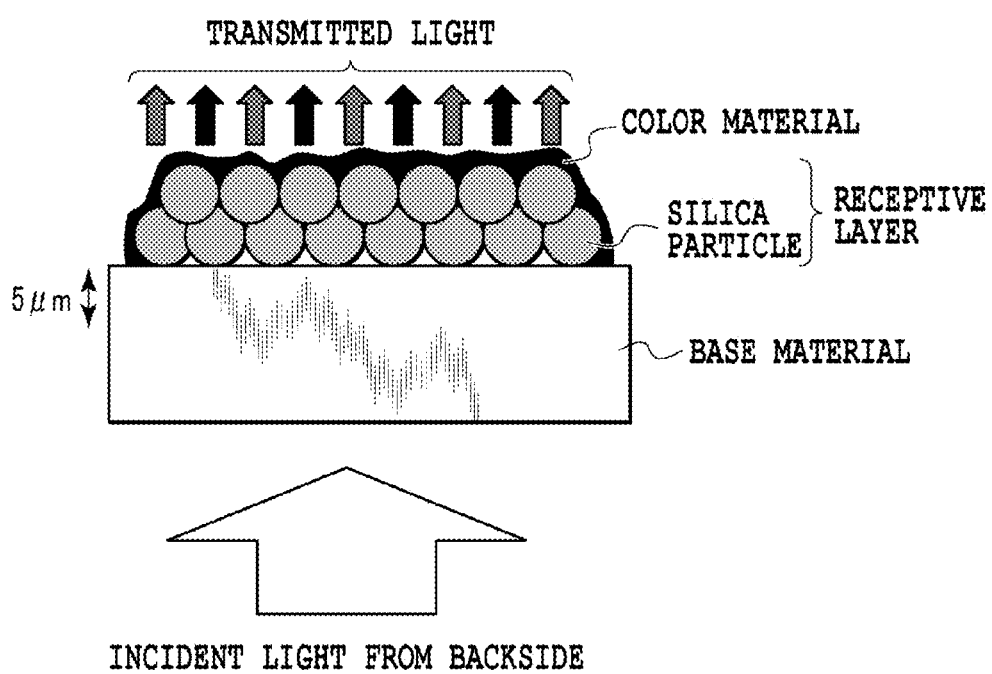
Figure 12A:
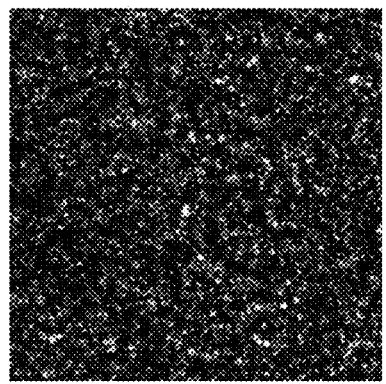
FIGS. 12A and 12B are diagrams showing examples of two-dimensional measurement results obtained by measuring the amount of transmitted light of the portion of the determination image printed using MK1.
Figure 12B:
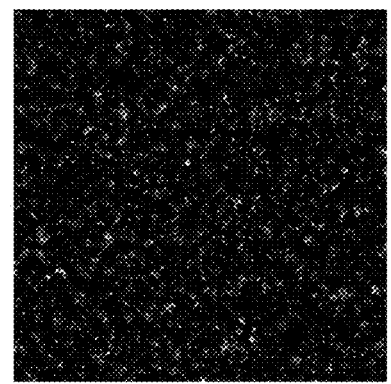

In the surface characteristics determination processing at step 703, the transmittance of the printing medium on which the determination image is printed is found, and from the transmittance that has been found, the surface characteristics (here, the deposition density of receptive layer particles) of the printing medium are estimated, and thereby, the printing medium is determined. FIGS. 11A and 11B are diagrams explaining the way of thinking at the time of estimating the deposition density of receptive layer particles from the transmittance, showing the way the light incident on the backside of the base material passes through the receptive layer and the color material. Each arrow indicates the transmitted light at each position and a difference in the density of the color represents a difference in the amount of light that passes through. In other words, the arrow in the denser color indicates that the amount of light that passes through is smaller and the arrow in the paler color indicates that the amount of light that passes through is larger. FIG. 11A shows the case of the printing medium of type whose deposition density of receptive layer particles is low and the color material has permeated among the particles. In this case, the transmitted light is divided into the light (indicated by the arrow in the dense color) that passes through both the color material and the particle and the light (indicated by the arrow in the pale color) that passes through only the particle and the amount of the light that passes through only the particle is not small, and therefore, the transmittance will be high. FIG. 11B shows the case of the printing medium of type whose deposition density of receptive layer particles is high and in this case, the color material does not permeate among the particles and the particles are covered by the color material so as to shield the entire surface of the printing medium. In this case the transmitted light is uniform (difference in the color of the arrow is slight) regardless of the position and the transmitted light amount is small on the whole, and therefore, the transmittance will be low. FIGS. 12A and 12B are diagrams showing examples of the two-dimensional measurement results obtained by measuring the amount of transmitted light of the portion of the determination image printed by using MK1 (matte black 1). FIG. 12A corresponds to FIG. 11A and because the deposition density of receptive layer particles is low, the amount of transmitted light is large, and therefore, the image is light on the whole. FIG. 12B corresponds to FIG. 11B and because the deposition density of receptive layer particles is high, the amount of transmitted light is small, and therefore, the image is dark on the whole compared to that in FIG. 12A.

The difference in the amount of transmitted light due to the difference in the deposition density of receptive layer particles as described above results from the fact that the amount of light that passes through the printing medium and reaches the inside thereof is larger than the amount of light that diffuses in the case where light enters the side of the printing medium whose refractive index is low compared to that of the color material. In the case where light enters the side of the color material whose refractive index is high compared to that of the printing medium as in the conventional technique, the amount of light that diffuses becomes larger than the amount of light that passes through the color material and reaches the inside thereof, and therefore, it will become difficult to accurately measure the transmittance.

As above, in order to determine the deposition density of fine particles constituting the receptive layer in coated paper, such as matte paper, in a simpler manner, the inventors of the present invention have found out the determination method based on the amount of transmitted light as a result of intensive research. In the schematic diagram in FIGS. 11A and 11B, the shape and size of the receptive layer particles are uniform, but the example is not limited to this. For example, even in the case where the shape and size of the particles vary, on a condition that gaps occur among particles depending on the deposition density, the same trend is observed, and therefore, application is similarly possible.

Figure 13:
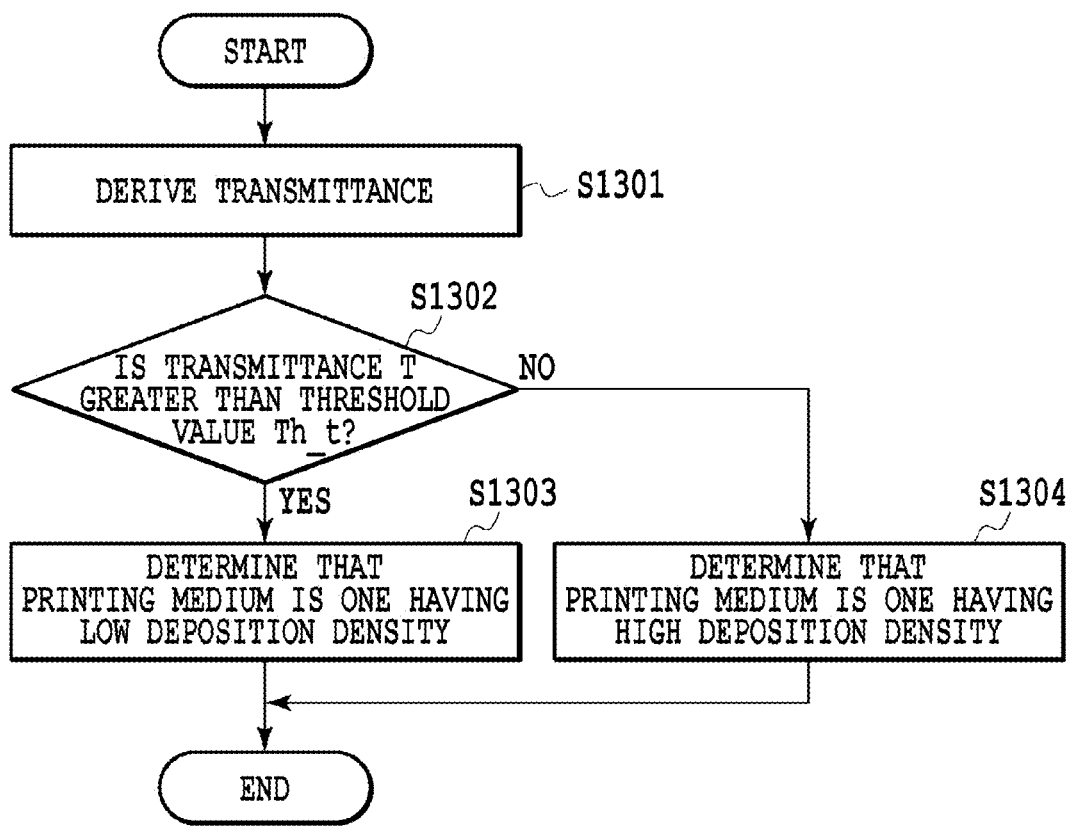
FIG. 13 is a flowchart showing a flow of specific processing in surface characteristics determination processing according to the first embodiment.

FIG. 13 is a flowchart showing a flow of specific processing in the surface characteristics determination processing according to the present embodiment.

At step 1301, the printing medium determination apparatus 110 finds a transmittance T of the printing medium on which the determination image is printed based on the transmitted light information acquired at step 702 described previously. It is possible to find the transmittance T by using an expression (1) below from the two kinds of transmitted light amounts (Y trans_paper and Y trans_color) included in the transmitted light information.

$$\text{Transmittance } T = Y\text{trans\_color} / Y\text{trans\_paper} \qquad \text{expression (1)}$$

For example, it is assumed that the two kinds of transmitted light amounts acquired at step 702 are Y trans_paper: 23.87 and Y trans_color: 0.25. In this case, the transmittance T will be 0.010 from the above-described expression (1). Similarly, it is assumed that the two kinds of transmitted light amounts acquired at step 702 are Y trans_paper: 13.60 and Y trans_color: 0.58. In this case, the transmittance T will be 0.043 from the above-described expression (1).

At step 1302, the printing medium determination apparatus 110 compares the transmittance T that has been found and a threshold value Th_t prepared in advance and determines whether the transmittance T is greater than the threshold value Th_t. In this case, as the threshold value Th_t, it is recommended to prepare recording media (samples) having various surface characteristics, to acquire the previously-described transmitted light information by using these sample and to derive the transmittance, and to determine and hold an appropriate value (e.g., 0.027) in advance. In the case where the transmittance T that has been found is greater than the threshold value Th_t as the result of the determination, the processing proceeds to step 1303. On the other hand, in the case where the transmittance T that has been found is equal to or less than the threshold value Th_t, the processing proceeds to step 1304. In the case where the threshold value Th_t is 0.027, on a condition that the above-described transmittance T is 0.010, the processing proceeds to step 1304 and on a condition that the above-described transmittance T is 0.043, the processing proceeds to step 1303 as a result. It may also be possible to input, for example, a value that a user has measured separately as the threshold value Th_t through the input unit 103 instead of holding the threshold value Th_t in advance.

At step 1303, the printing medium determination apparatus 110 determines that the surface of the printing medium is not covered sufficiently by the color material and that the printing medium is a printing medium of the kind whose deposition density of particles constituting the receptive layer is low.

At step 1304, the printing medium determination apparatus 110 determines that the surface of the printing medium is covered sufficiently by the color material and that the printing medium is a printing medium of the kind whose deposition density of particles constituting the receptive layer is high.

This determination results are input to the host 100 from the determination apparatus IF 105 as deposition density information. For example, in the case where the deposition density of receptive layer particles is low, a flag "d_flg: 0", or in the case where the deposition density of receptive layer particles is high, a flag "d_flg: 1" is input to the host 100 via the determination apparatus IF 105 and then is sent to the control unit 108 (see FIG. 2).

In the present embodiment, the kind of the printing medium is classified into two kinds (the kind whose deposition density is low and the kind whose deposition density is high), but it may also be possible to classify the kind into three kinds (low, medium, high) by preparing, for example, the two threshold values Th_t. Further, in the present embodiment, the printing medium is determined based on the deposition density of receptive layer particles by comparing the transmittance that has been found and the threshold value, but the determination is not limited to this. For example, it may also be possible to prepare a table in which the transmittance and the deposition density of receptive layer particles are associated with each other and to determine the kind of the printing medium corresponding to the transmittance that has been found by referring to the table. Alternatively, it may also be possible to determine the kind of the printing medium by calculating the deposition density of receptive layer particles by multiplying the transmittance that has been found by a predetermined coefficient.

<About Printing Control Processing>

In the printing control processing at step 704, appropriate printing processing in accordance with a purpose is performed on image data selected by a user (selected from a plurality of pieces of image data stored in the HDD 104) in accordance with the determined kind of the printing medium. Various kinds of image processing (conversion into multivalued data, resolution conversion, color matching, color conversion, halftoning, multipath division, etc.) are performed on the image data on which the printing processing is to be performed and the image data is converted into final print data.

Figure 14:
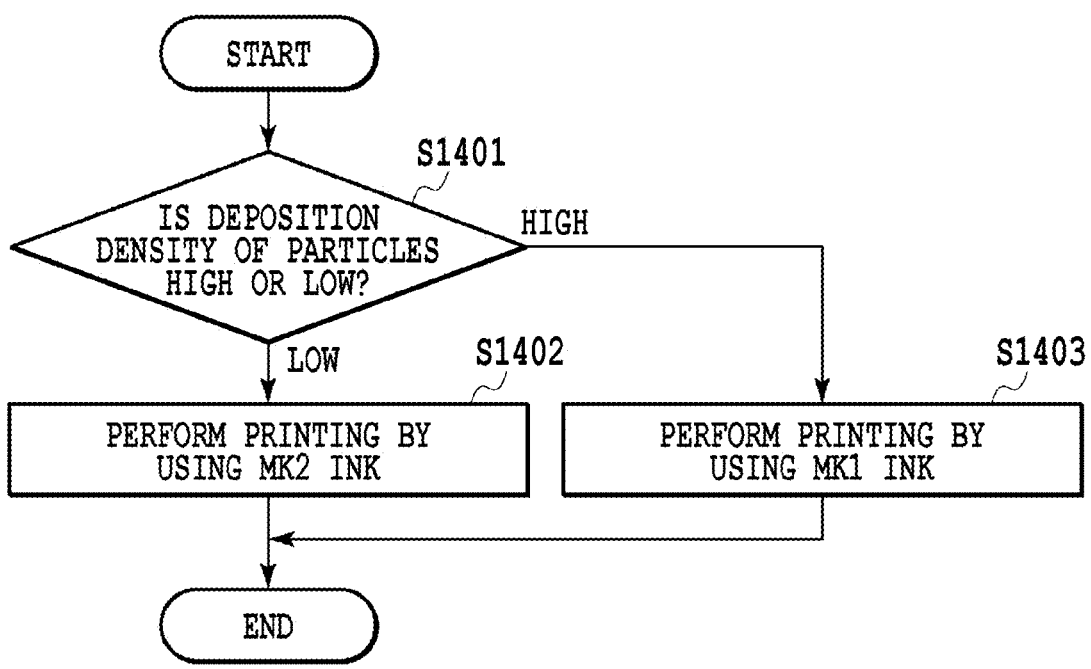
FIG. 14 is a flowchart showing a flow of specific processing in printing control processing according to the first embodiment.

FIG. 14 is a flowchart showing a flow of specific processing in the printing control processing according to the present embodiment. In this printing control processing, printing control in accordance with a purpose is performed on print data, and in the present embodiment, an aspect is shown in which the improvement in the density in a dark area of an image is aimed at and the ink that is used is switched to another in accordance with the deposition density of receptive layer particles estimated by the surface characteristics determination processing.

At step 1401, the control unit 108 allocates processing based on the determination results in the previously-described surface characteristics determination processing, i.e., based on the flag (d_flg: 0 or d_flg: 1) as deposition density information. In the case of the flag (d_flg: 0) indicating that the deposition density is low, the processing proceeds to step 1402. On the other hand, in the case of the flag (d_flg: 1) indicating that the deposition density is low, the processing proceeds to step 1403.

At step 1402, the control unit 108 prints the print data on the printing medium by using the MK2 ink having a relatively high viscosity.

At step 1403, the control unit 108 prints the print data on the printing medium by using the MK1 ink having a relatively low viscosity (standard viscosity).

FIGS. 15A to 15C are schematic diagrams showing how the ink fixes onto the printing medium as the results of performing the printing processing as described above. First, FIG. 15A shows a fixed state of the ink in the case where an image is printed on the printing medium whose deposition density of receptive layer particles is low by using the MK1 ink having a standard viscosity. It is known that the ink, which is the color material, has fallen into gaps among the receptive layer particles and the amount of ink that remains on the surface of the receptive layer is small. In the case where the ink, which is the color material, has fallen into gaps among the receptive layer particles, many regions in which the density is insufficient are produced locally, and therefore, the density reduces. FIG. 15B shows a fixed state of the ink in the case where an image is printed on the printing medium whose deposition density of receptive layer particles is low by using the MK2 ink having a high viscosity. In this case, it is known that the ink, which is the color material, does not fall easily into gaps among the receptive layer particles and a large amount of ink remains on the surface of the receptive layer. In this manner, it is possible to prevent a reduction in density because a large amount of ink, which is the color material, remains on the surface of the receptive layer. FIG. 15C shows a fixed state of the ink in the case where an image is printed on the printing medium whose deposition density of receptive layer particles is high by using the MK1 ink having a standard viscosity. In this case, the receptive layer particles are dense, and therefore, the ink can fix to the portions in the vicinity of the surface of the receptive layer even by the ink having a standard viscosity. In the case where the ink having a viscosity higher than the standard viscosity is used on the printing medium whose deposition density of receptive layer particles is high, there may occur trouble in image quality that the ink overflows the receptive layer, and therefore, it is preferable to use the ink having a standard viscosity on the printing medium whose deposition density of receptive layer particles is high.

As described above, by performing control so that an image is formed by using the ink suitable to the deposition density of receptive layer particles, it is possible to improve the image density.

In the above-described embodiment, the case is described where the ink that is used is switched to another so as to prevent a reduction in density in a dark area of an image. However, for example, in the case of a printing apparatus equipped with only one kind of matte black ink, such switching control as described above cannot be performed. In this case, it may also possible to prompt a user to determine whether to continue printing by, for example, displaying a message to the effect that the desired density cannot be achieved before the printing processing is performed. Alternatively, it may also be possible to perform control to change the number of paths in multipath printing, i.e., to perform control so as to increase the number of paths in the case where it is desired to increase the density (on the contrary, the number of paths is reduced in the case where it is desired to reduce the density). The reason is that as the number of paths increases, the amount of ink that is ejected at a time is reduced, and therefore, the amount of ink that permeates into the inside of the receptive layer is not so large and in addition to this, the ink that is ejected from the next path is blocked from permeating into the inside of the receptive layer by the ink that has been left and fixed on the surface, and as a result of that, a larger amount of ink is left on the surface.

In the case of a printing apparatus that includes another ink tank so as to be able to eject a reactive agent to cause the ink to fix on the paper surface, it may also be possible to perform control to change the amount of reactive agent that is used in accordance with the deposition density of receptive layer particles. In other words, it may also be possible to perform control so as to increase the amount of reactive agent that is used in the case where the deposition density is low and to reduce the amount of reactive agent that is used in the case where the deposition density is high.

In the present embodiment, the deposition density of the receptive layer is estimated by printing a determination image, acquiring transmitted light information, and performing surface characteristics determination processing, but there is a case where the information on the deposition density of the receptive layer is known in advance or where the information can be obtained by downloading etc. the information from an external network. In such a case, it may also be possible to omit the printing of the determination image (step 701) to the surface characteristics determination processing (step 704) and to perform the printing control processing (step 703).

Further, in the printing control processing in the present embodiment, printing control in accordance with the printing medium is performed by using the deposition density information (flag) generated in the surface characteristics determination processing, but the processing is not limited to this. For example, it may also be possible for a user to save in advance the information on the deposition density that has been obtained by separately measuring the transmittance in the same method, and to input the information through the input unit 103 at the time of printing, and thus, printing control is performed based on the input deposition density information.

Furthermore, in the present embodiment, the printing control aiming at the improvement in image density is described, but printing control aiming at different purposes may be included in the category of the present invention. For example, there is a case where the ink on a printed printing medium is peeled off by a hand rubbing the surface thereof and the ink moves to the hand. How much ink is peeled off and moves to an object in the case where the paper is rubbed by the object is referred to as rubfastness (index indicating the resistance to the rubbing on the ink surface). Then, it is known that the more the ink that has fixed on the surface of the receptive layer, the lower the rubfastness is (ink is easily peeled off). In other words, fixing an ink on the receptive layer surface in order to aim at the improvement in image density will bring a state where the ink is easily peeled off and the rubfastness is reduced. Consequently, in the case where the improvement in rubfastness is aimed at, it is recommended to perform control so as to cause the ink to permeate into the paper more deeply, i.e., to perform control so that in the case where the deposition density of receptive layer particles is higher, an ink having a lower viscosity is used.

As described above, according to the present embodiment, the deposition density of fine particles constituting the receptive layer of a printing medium is simply estimated from the transmittance of the printing medium. Then, in accordance with the estimated deposition density, the printing control in accordance with a purpose is implemented.

Second Embodiment

In the first embodiment, the aspect is explained in which the transmittance is found by acquiring information on the amount of light that passes through the printing medium and based on the transmittance that has been found, the deposition density of particles constituting the receptive layer is estimated and thereby the kind of the printing medium is specified. Next, an aspect is explained as a second embodiment, in which as transmitted light information, distribution information on light that passes through a printing medium is acquired, then, a period of unevenness of the deposition density of the receptive layer is found, and from the period of unevenness that has been found, the deposition density of receptive layer particles is estimated and the kind of the printing medium is specified. Explanation of the portions in common to those of the first embodiment is simplified or omitted and different points are explained mainly.

<About Acquisition of Transmitted Light Information>

In the acquisition processing of transmitted light information in the first embodiment, the transmitted light amount Y trans_color in the entire region in which the determination image is printed and the transmitted light amount Y trans_paper in the region in which the determination image is not printed are acquired. In the acquisition processing of transmitted light information in the present embodiment, distribution information on light that passes through a printing medium on which a determination image is printed is acquired from the positional relationship between the pattern of the determination image and the line sensor 503. In detail, the region in which the determination image is printed is divided into meshes having a certain size and by causing the line sensor 503 to sequentially scan, the transmitted light amount of each mesh is acquired. Finer meshes will provide more detailed distribution information, leading to the derivation of an exact period of unevenness.

<About Surface Characteristics Determination Processing>

In the surface characteristics determination processing according to the present embodiment, from the transmitted light information (distribution information on light that passes through the region in which the determination image is printed) acquired by the above-described acquisition processing of transmitted light information, first, the component of the period of unevenness of the deposition density that depends on the receptive layer particle diameter is extracted. Then, by comparing the extracted component of the period of unevenness and a threshold value held in advance, the deposition density of receptive layer particles is estimated.

As explained by using FIGS. 11A and 11B in the first embodiment, light incident on the backside of the base material will become transmitted light uneven from position to position depending on the deposition density of receptive layer particles and the way the color material fixes. It is known that the period of unevenness depends on the receptive layer particle diameter. Consequently, in the present embodiment, from a fixed range of the particle diameter and the amplitude of the component of the period corresponding to the particle diameter, the deposition density of receptive layer particles is estimated. Here, the fixed range of the particle diameter refers to the size of an aggregation including one to a plurality of particles that can be supposed from the results of measuring in advance the surfaces of a plurality of kinds of recording media (here, matte paper, and indicates the range that can be identified by the line sensor 503. In the case where the optical resolution of the line sensor 503 is 19,200 dpi, in view of the sampling period, the fixed range of the particle diameter will be 3 μm or greater, which is the particle diameter that can be identified. In this manner, from the range that can be identified by the line sensor 503 and the range that is supposed from the results of measuring the surfaces of a plurality of kinds of matte paper, the target range of the particle diameter is determined.

Figure 16:
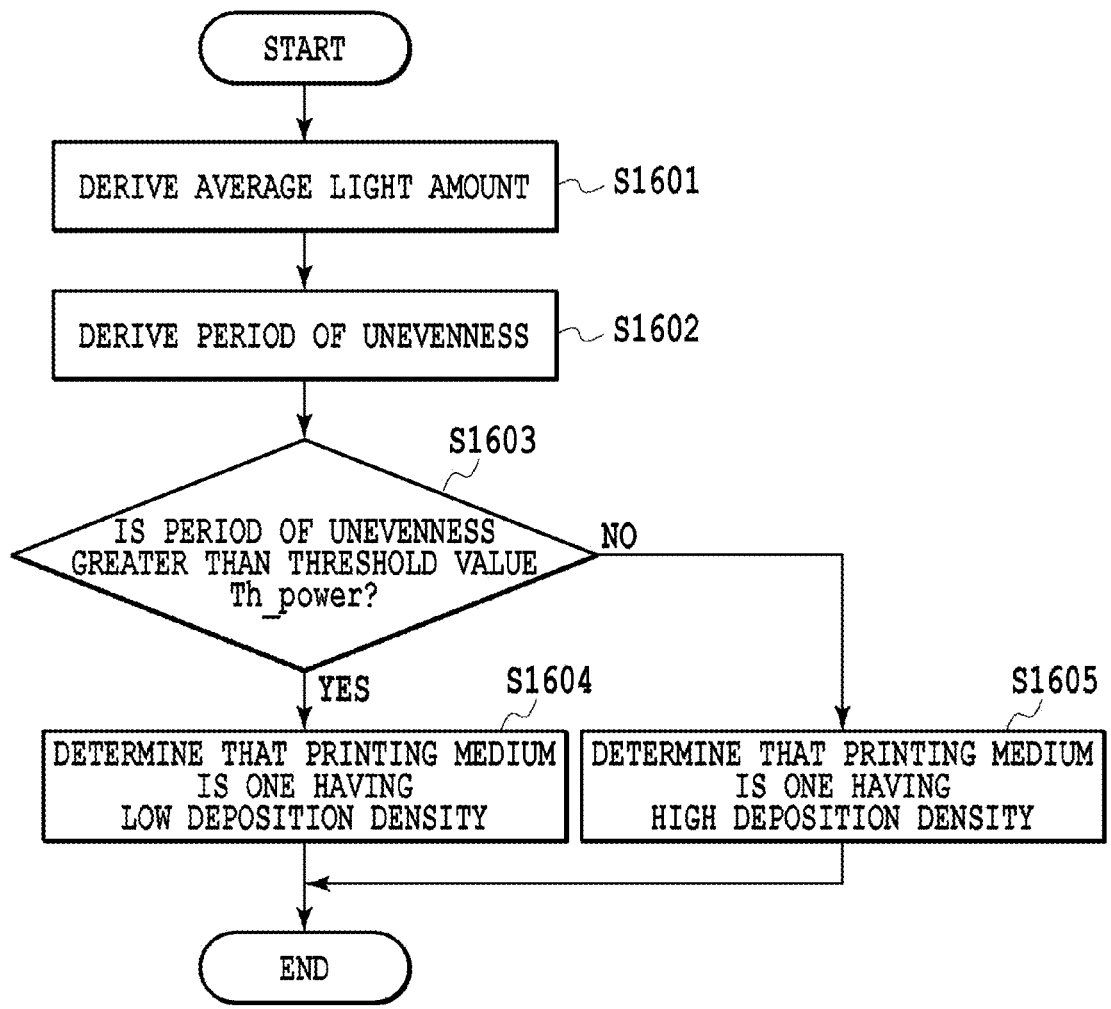
FIG. 16 is a flowchart showing a flow of specific processing in surface characteristics determination processing according to a second embodiment.

FIG. 16 is a flowchart showing a flow of specific processing in the surface characteristics determination processing according to the present embodiment.

Figure 17A:
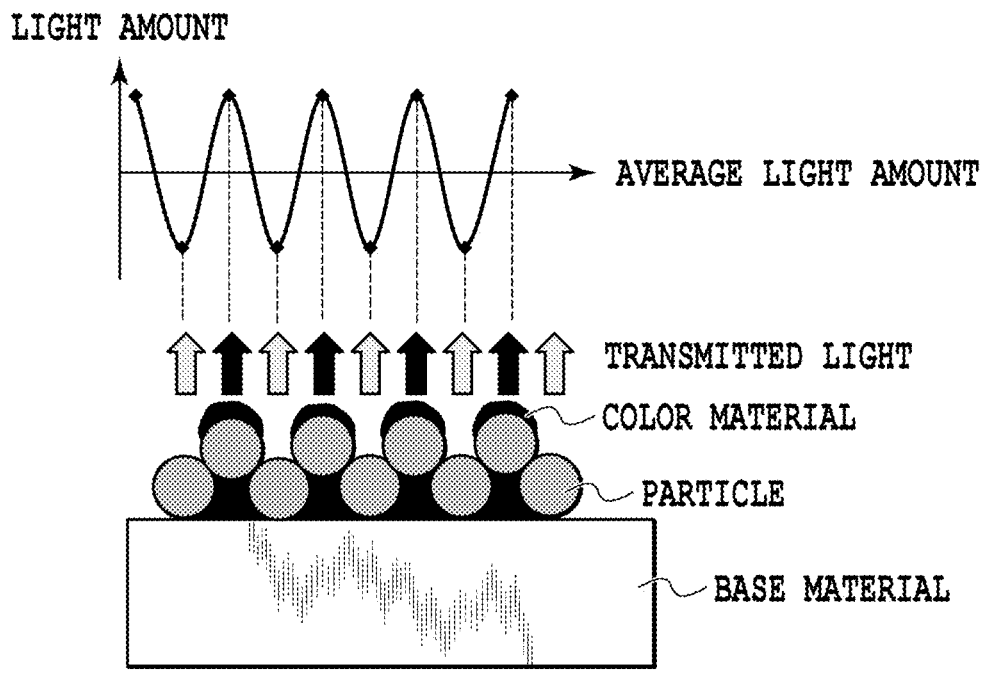
FIGS. 17A and 17B are diagrams showing the way an average light amount is found from distribution information on transmitted light, and FIG. 17A corresponds to the case where the deposition density of receptive layer particles is low and FIG. 17B corresponds to the case where the deposition density of receptive layer particles is high, respectively.
Figure 17B:
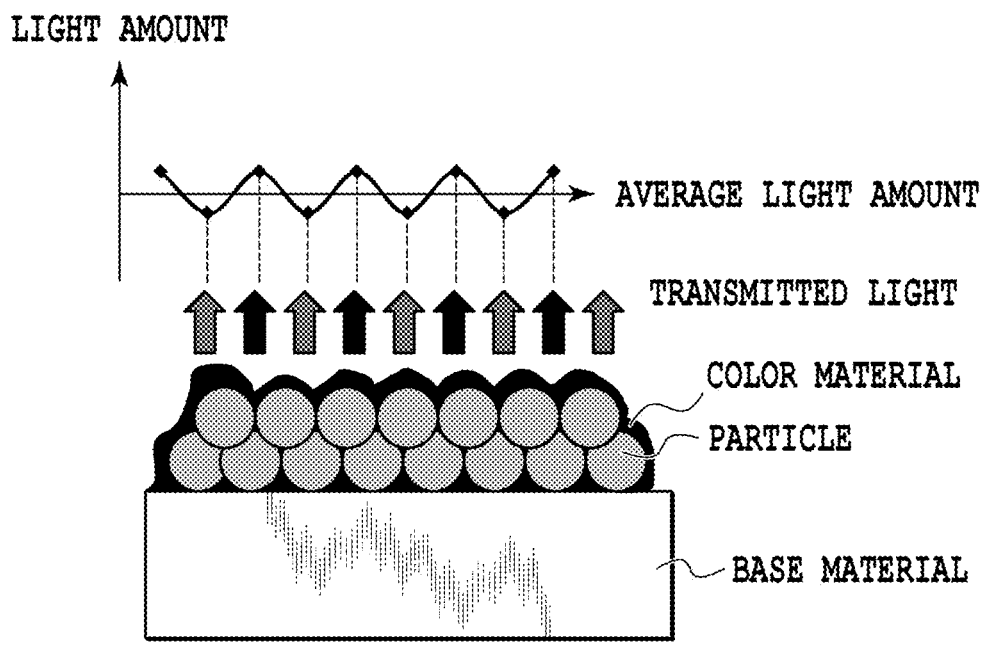

At step 1601, the printing medium determination apparatus 110 finds an average light amount from the distribution information on transmitted light acquired in the above-described acquisition processing of transmitted light information. Specifically, the total value of the transmitted light amount of each mesh is found and by dividing the total value that is found by the total number of meshes, the average light amount is obtained. FIGS. 17A and 17B are diagrams showing the way the average light amount is found from the distribution information on transmitted light, and FIG. 17A corresponds to the case where the deposition density of receptive layer particles is low and FIG. 17B corresponds to the case where the deposition density of receptive layer particles is high, respectively.

Figure 18A:
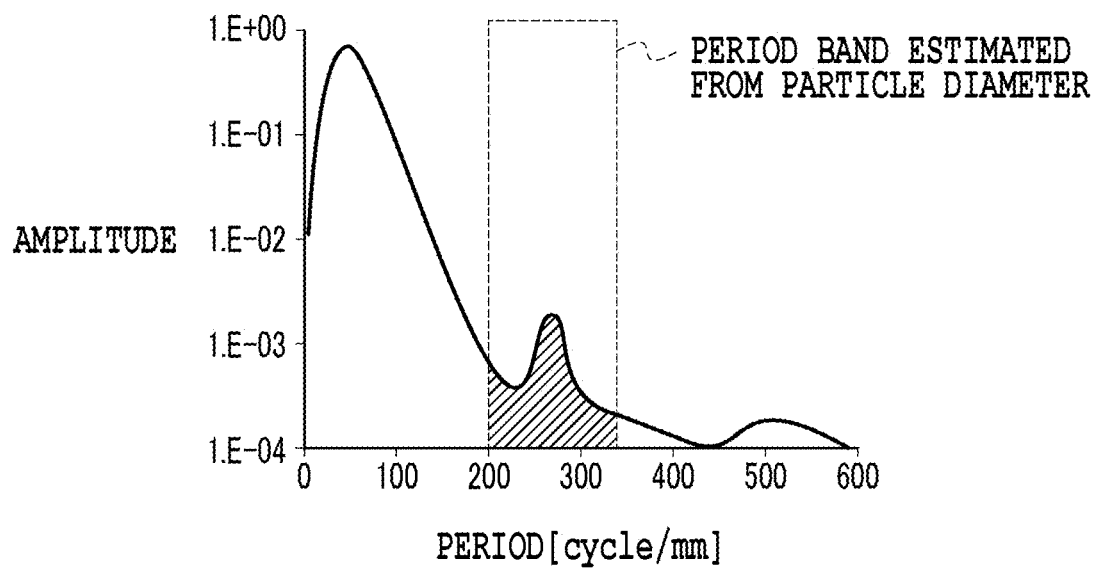
FIGS. 18A and 18B are diagrams showing a graph obtained by plotting an amplitude of each period obtained by Fourier transformation, also visually showing a period band corresponding to a fixed range of particle diameter, and FIG. 18A corresponds to the case where the deposition density of receptive layer particles is low and FIG. 18B corresponds to the case where the deposition density of receptive layer particles is high, respectively.
Figure 18B:
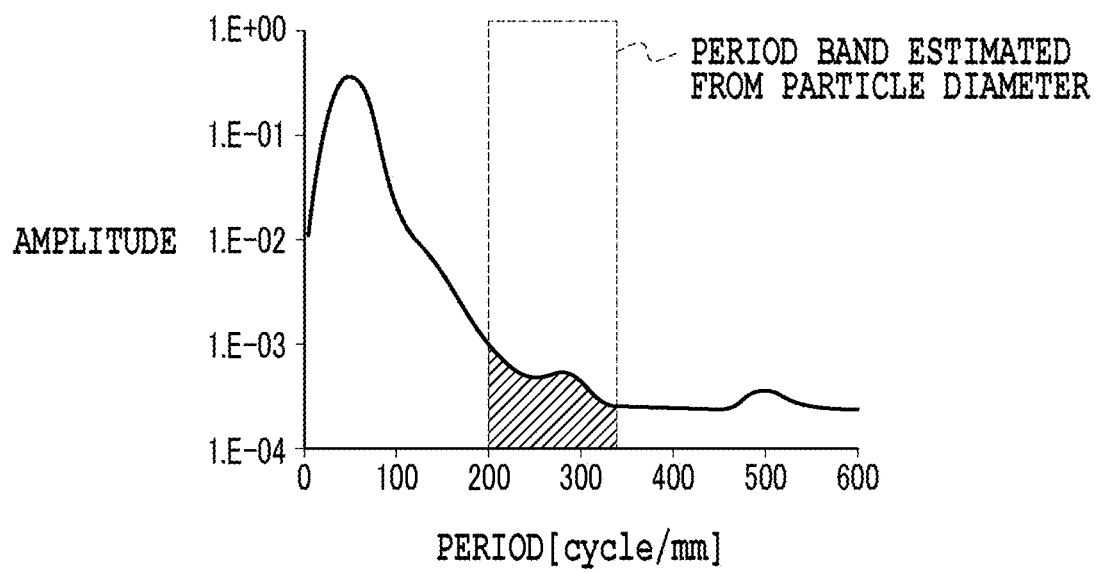

At step 1602, the printing medium determination apparatus 110 extracts the component of the period of unevenness of the deposition density of the receptive layer. Specifically, as follows. First, based on the average light amount obtained at step 1601, data indicative of a ratio (hereinafter, called "ratio data") of the transmitted light amount at each position indicated by the distribution information on transmitted light to the average light amount is generated. For example, in the case where the transmitted light amount at a certain mesh is 0.3 and the average light amount is 0.2, the ratio at the position (mesh) is 0.3÷0.2=1.5. The ratio such as this is found at each position (each mesh). Next, the generated ratio data is converted into an amplitude for each period by using the publicly-known Fourier transformation and the amplitude value of the period band corresponding to the fixed range of the particle diameter prepared in advance is found. FIGS. 18A and 18B show diagrams of graphs obtained by plotting the amplitude for each period obtained by Fourier transformation, visually showing the period band corresponding to the fixed range of the particle diameter, and FIG. 18A corresponds to the case where the deposition density of receptive layer particles is low and FIG. 18B corresponds to the case where the deposition density of receptive layer particles is high, respectively. In FIGS. 18A and 18B, the integral value of the portion indicated by slashes is the amplitude value. Finally, a total value Power_g of the obtained amplitude values is obtained. This total value Power_g is the component of the period of unevenness.

At step 1603, the printing medium determination apparatus 110 determines whether the total value Power_g as the component of the period of unevenness derived at step 1602 is greater than a threshold value Th_power prepared in advance. For example, it is assumed that the total value Power_g in the case where the deposition density of receptive layer particles is low is about 0.322 and the total value Power_g in the case where the deposition density of receptive layer particles is high is about 0.300. In this case, the threshold value Th_power is set to, for example, 0.031. The threshold value Th_power such as this is derived and held in advance by using the recording media having a plurality of surface characteristics as in the case of the threshold value Th_t in the first embodiment. In the case where the total value Power_g is greater than Th_power, the processing proceeds to step 1604. On the other hand, in the case where the total value Power_g is smaller than Th_power, the processing proceeds to step 1605.

At step 1604, the printing medium determination apparatus 110 determines that the surface of the printing medium is not covered sufficiently by the color material and that the printing medium is one of the kind whose deposition density of particles constituting the receptive layer is low.

At step 1605, the printing medium determination apparatus 110 determines that the surface of the printing medium is covered sufficiently by the color material and that the printing medium is one of the kind whose deposition density of particles constituting the receptive layer is high.

Then, as in the first embodiment, the results of the determination processing are input to the host 100 from the determination apparatus IF 105 as deposition density information.

As above, in the present embodiment, the kind of the printing medium is determined based on the period of unevenness of the transmitted light amount derived from the distribution information on transmitted light at each position of the printing medium.

Instead of finding the amplitude of the specific period band from the distribution information on transmitted light, it may also be possible to generate a histogram of the transmitted light amount and to determine the kind of the printing medium by regarding the shape of the histogram as the feature amount. For example, it is possible to determine that the deposition density is high in the case where the number of positions where the transmitted light amount is small is comparatively large.

In the present embodiment, the kind of the printing medium is determined by finding the total value of the amplitude values of the specific period band and by comparing the total value with the threshold value Th_power, but it may also be possible to determine the kind of the printing medium by comparing the amplitude value of each period with a predetermined threshold value and by determining whether the number of amplitude values that exceed the threshold value is equal to or greater than a fixed number.

Further, in the surface characteristics determination processing, it may also be possible to estimate the surface characteristics by using both the transmittance according to the first embodiment and the distribution information on transmitted light according to the present embodiment as the transmitted light information.

Third Embodiment

In the first and second embodiments, the kind of a printing medium is determined by estimating the deposition density of receptive layer particles based on only information on transmitted light and it is possible to determine the recording media into the low deposition density group in FIGS. 2 (*a*) and (*c*) described previously and the high deposition density group in FIGS. 2 (*b*) and (*d*). However, in the first and second embodiments, more detailed determination is difficult to perform. In the case where more detailed determination of the kind of a printing medium can be performed, it is made possible to more appropriately perform printing control in accordance with a purpose, such as the improvement in density and the improvement in rubfastness.

Next, an aspect is explained in which not only the deposition density of receptive layer particles but also the particle diameter thereof are estimated as the surface characteristics by using information on reflected light, in addition to the information on transmitted light, and thereby, it is made possible to perform more detailed determination (e.g., determination of whether a printing medium belongs to the low deposition density group in FIG. 2 (*a*) described previously or to that in FIG. 2 (*c*)). Explanation of the portions in common to those of the first and second embodiments is simplified or omitted and different points are explained mainly.

Figure 19B:
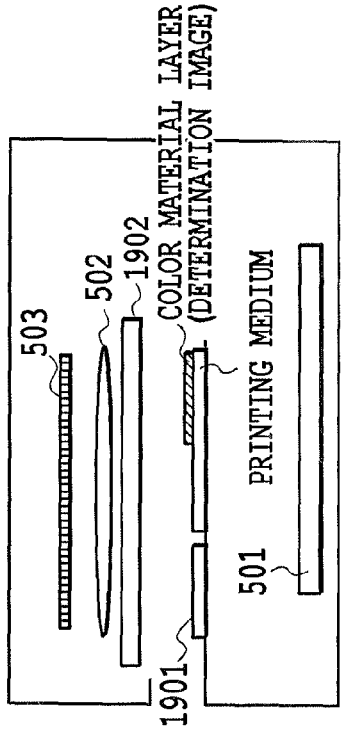
FIGS. 19A to 19C are diagrams explaining an outline of a printing medium determination apparatus according to a third embodiment.
Figure 19C:
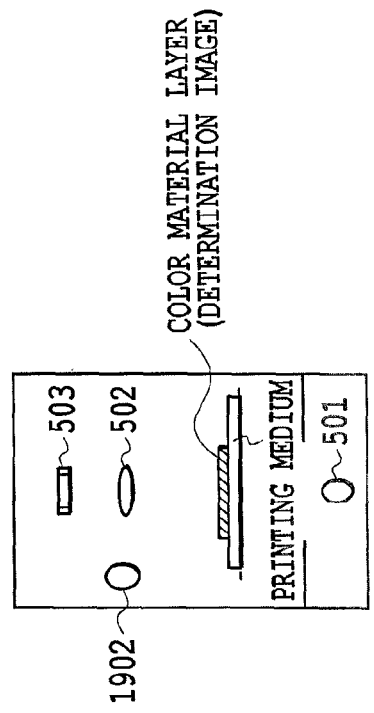
Figure 19A:
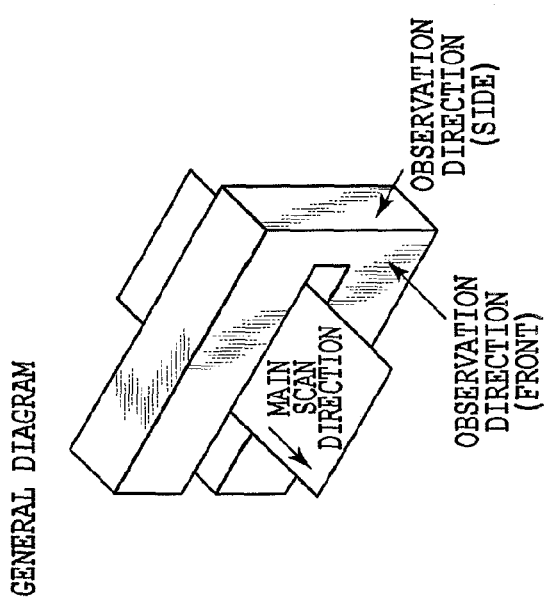

FIGS. 19A to 19C are diagrams explaining an outline of the printing medium determination apparatus 110 according to the present embodiment, and FIG. 19A is a general diagram, FIG. 19B is a schematic section diagram from the front, and FIG. 19C is a schematic section diagram from the side. As shown in FIG. 19B, in addition to the configuration of the first embodiment (see FIGS. 5A to 5C), a reference plate 1901 is provided, which is arranged so as to be put side by side in the sub scan direction with a printing medium that is conveyed. The reference plate 1901 is used as a reference at the time of acquiring reflected light information, to be described later, and is made of a material, such as ceramics, whose optical characteristics change slightly over time. Further, it may also be possible to provide a shutter (not shown) for preventing stain. As shown in FIG. 19C, a second white fluorescent lamp 1902 is arranged in a direction that forms an angle of 45 degrees with a normal line that connects the printing medium and the line sensor 503 downstream in the main scan direction. Reflected light traveling in the normal line direction, which is light irradiated from the white fluorescent lamp 1902 and reflected from the printing medium (or the printing medium and the color material layer), is condensed by the condensing lens 502. The optical path length of the condensed light is adjusted by a mirror lens, not shown, and the condensed light is received by the line sensor 503 and the light amount thereof is detected.

Figure 20:
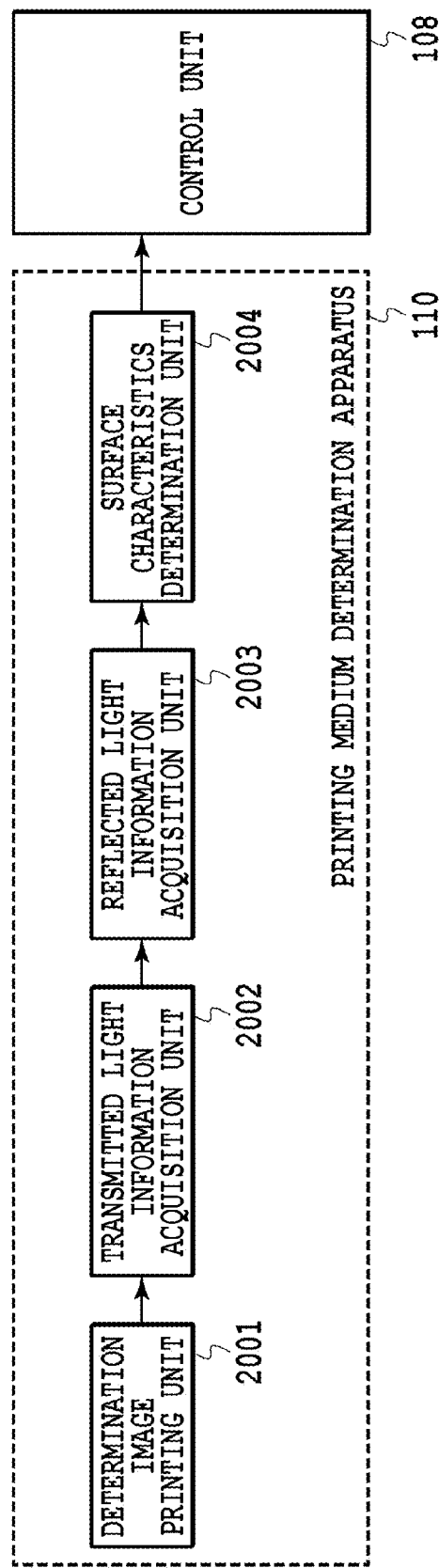
FIG. 20 is a block diagram showing a function configuration of the printing medium determination apparatus according to the third embodiment.

FIG. 20 is a block diagram showing a function configuration of the printing medium determination apparatus 110 according to the present embodiment. The printing medium determination apparatus 110 includes a determination image printing unit 2001, a transmitted light information acquisition unit 2002, a reflected light information acquisition unit 2003, and a surface characteristics determination unit 2004. The final output (determination results) of the printing medium determination apparatus 110 is sent to the control unit 108 via the determination apparatus IF 105.

<Flow of Processing in the Present Embodiment>

Figure 21:
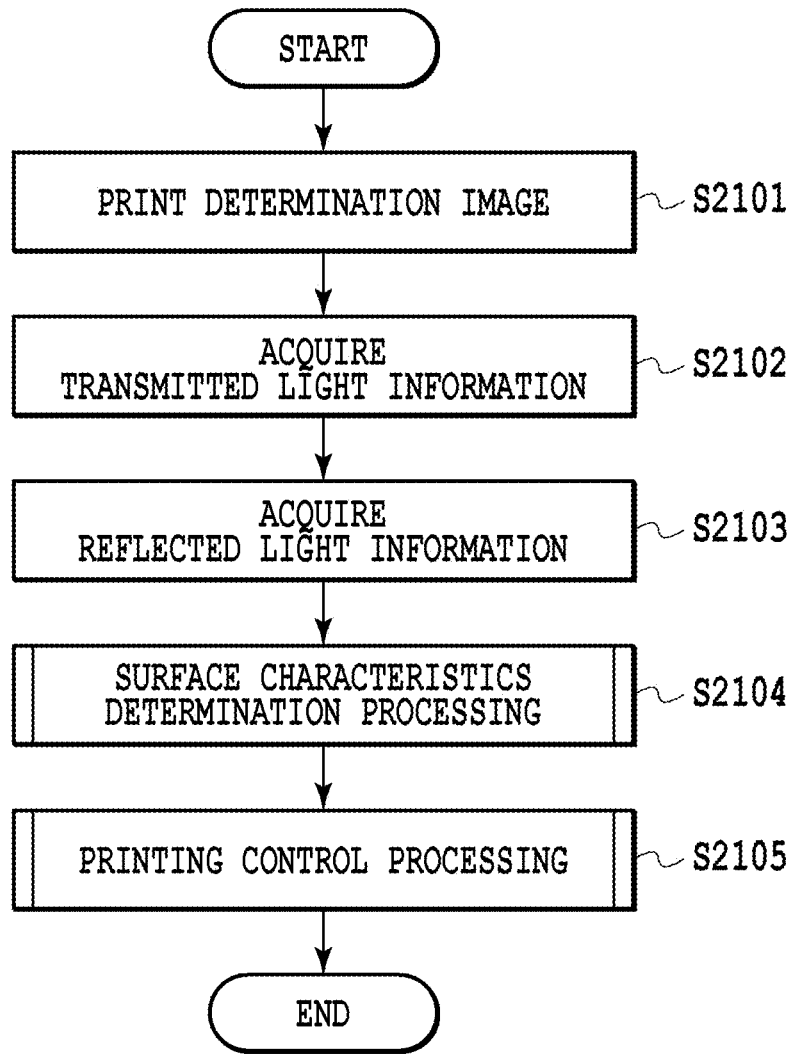
FIG. 21 is a flowchart showing a flow of each piece of the processing from printing of a printing medium determination image to printing control processing based on the determination results according to the third embodiment.

In the case where a request to perform processing to determine the kind of a printing medium is input from the input unit 103 by a user, the input unit 103 notifies the CPU 101 of the start of determination processing. The CPU 101 having received the notification notifies the printing medium determination apparatus 110 of the start of processing and performs processing below. FIG. 21 is a flowchart showing a flow of each piece of the processing from the printing of a printing medium kind determination image to the printing control processing based on the determination results according to the present embodiment.

Step 2101 and step 2102 are the same as step 701 and step 702 in the flowchart in FIG. 7 according to the first embodiment. In other words, first, a determination image is printed at a predetermined position of a printing medium by the printing apparatus 120 (step 2101) and next, transmitted light information of the printing medium is acquired by the printing medium determination apparatus 110 (step 2102).

At step 2103, the CPU 101 gives instructions to acquire reflected light information to the printing medium determination apparatus 110. Upon receipt of the instructions, the printing medium determination apparatus 110 causes the second white fluorescent lamp 1902 to emit light and acquires reflected light information of the printing medium. Here, as the reflected light information, information on reflected light that is reflected from the reference plate 1901 and information on reflected light that is reflected from the color material layer formed on the printing medium are acquired. After acquiring the reflected light information, the printing medium determination apparatus 110 notifies the CPU 101 of the completion of the acquisition of reflected light information.

At step 2104, the CPU 101 gives instructions to perform processing to determine the surface characteristics of the printing medium to the printing medium determination apparatus 110. Upon receipt of the instructions, the printing medium determination apparatus 110 finds the deposition density of receptive layer particles and the particle diameter as the surface characteristics based on the transmitted light information acquired at step 2102 and the reflected light information acquired at step 2103 and performs processing to determine the kind of the printing medium. After completing determination, the printing medium determination apparatus 110 notifies the control unit 108 of the determination results.

At step 2105, the control unit 108 performs control processing of printing (printing control processing) in accordance with the kind of the printing medium based on the received determination results.

In the following, each process of the processing is explained in detail.

<About Acquisition of Reflected Light Information>

Figure 22A:
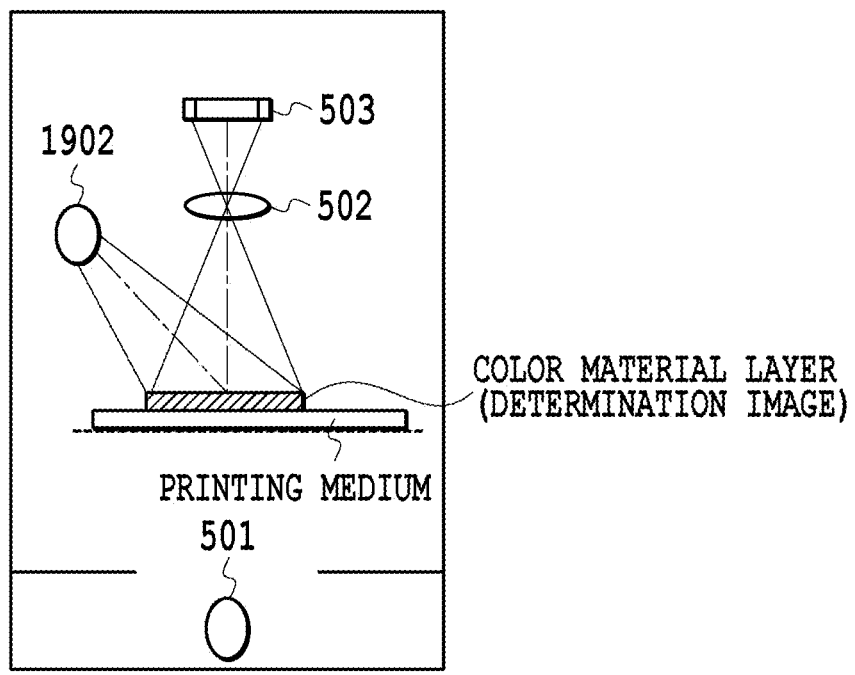
FIG. 22A is a diagram explaining the way the amount of reflected light from the determination image (color material layer) on the printing medium is acquired.
Figure 22B:
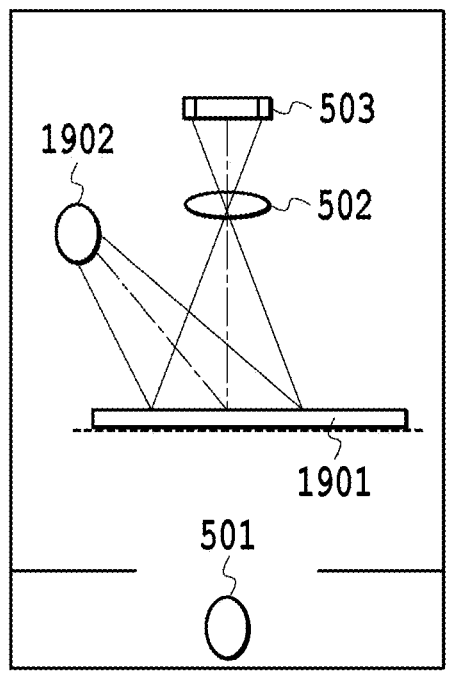
FIG. 22B is a diagram explaining the way the amount of light reflected from the reference plate is acquired.

As described above, in the acquisition processing of reflected light information at step 2103, two kinds of information (the amount of light reflected from the reference plate 1901 and the amount of light reflected from the region where the color material layer exists on the printing medium) are acquired. FIG. 22A is a diagram explaining the way the amount of light reflected from the determination image (color material layer) on the printing medium is acquired and FIG. 22B is a diagram explaining the way the amount of light reflected from the reference plate is acquired.

In the case where the printing medium is conveyed, the printing medium determination apparatus 110 causes the second white fluorescent lamp 1902 to light up and receives light reflected from the reference plate 1901 and the color material layer on the printing medium by the line sensor 503. Then, as in the case of the transmitted light information, the above-described two kinds of information on the reflected light amount are acquired from the positional relationship with the line sensor 503. In detail, a sensor portion that receives light reflected from the reference plate 1901 is specified in the line sensor 503 and the amount of light detected at the specified sensor portion is taken to be an amount of reflected light Y ref_abs from the reference plate 1901. Similarly, a sensor portion that receives light reflected from the region where the color material layer exists on the printing medium is specified in the line sensor 503 and the amount of light detected at the specified sensor portion is taken to be an amount of reflected light Y ref_color from the color material layer on the printing medium.

<About Surface Characteristics Determination Processing>

In the surface characteristics determination processing at step 2104, the transmittance and the reflectance of the printing medium on which the determination image is printed are found, and the surface characteristics (the deposition density of receptive layer particles and the particle diameter) of the printing medium are estimated from the transmittance and the reflectance that have been found, and thereby, the printing medium is determined. The method for estimating the deposition density of receptive layer particles from the transmittance is the same as that of the first embodiment, and therefore, explanation is omitted and here, how the particle diameter of receptive layer particles is estimated from the reflectance is explained.

Figure 23A:
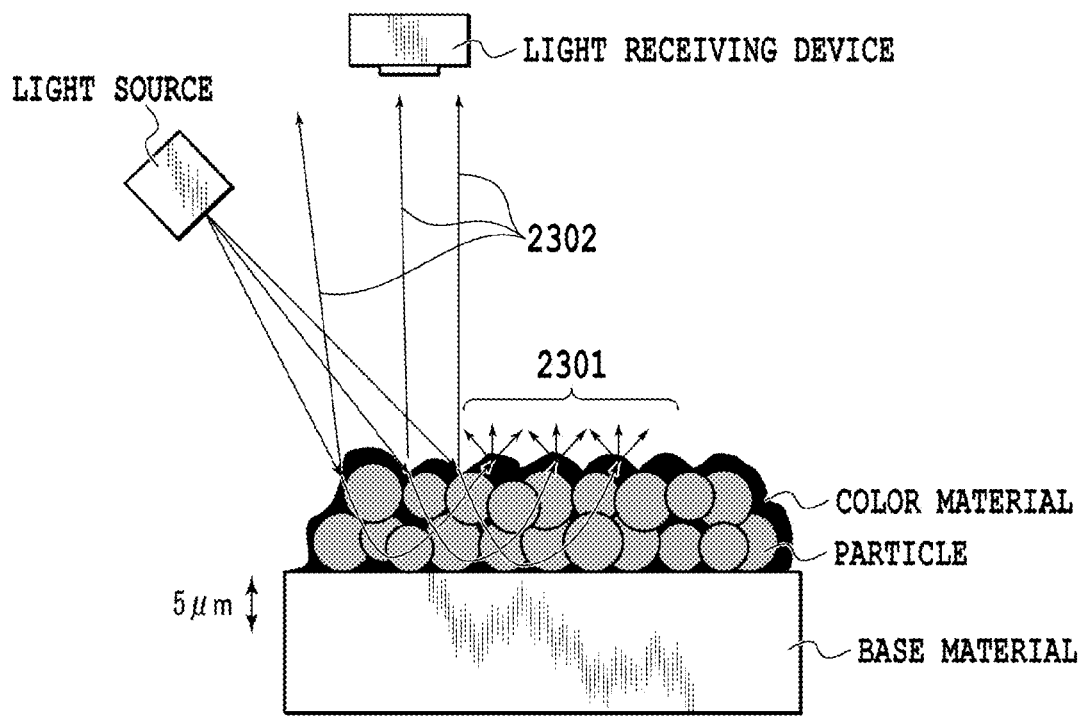
FIGS. 23A and 23B are diagrams showing how light from a light source diffuses on the surface of a printing medium.
Figure 23B:
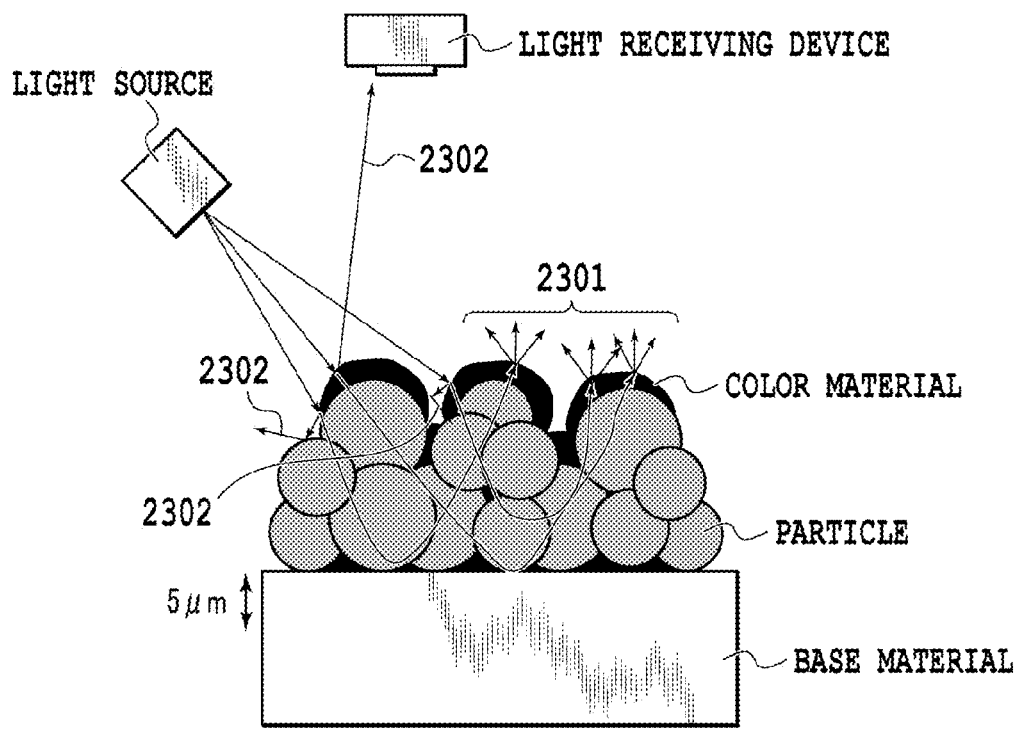

FIGS. 23A and 23B are diagrams showing how light from the light source (second white fluorescent lamp 1902) diffuses on the surface of the printing medium, and FIG. 23A explains the case where the receptive layer particle diameter is small and FIG. 23B shows the case where the receptive layer particle diameter is large. In FIG. 23A, it is known that in addition to light 2301 that has been reflected inside the color material layer and diffused on the surface of the color material layer, light 2302 that has been reflected on the surface of the color material layer is traveling toward the line sensor 503. On the other hand, in FIG. 23B, it is known that the light 2301 that has been reflected inside the color material layer and diffused on the surface of the color material layer is the same as in FIG. 23A, but the light 2302 that has been reflected on the surface of the color material layer attenuates due to the multiple reflection by the surface asperity and part of the reflected light does not reach the line sensor 503. In other words, in the case where the receptive layer particle diameter is large, the amount of light that is reflected on the surface and reaches the line sensor 503 is smaller than that in the case where the particle diameter is small, and therefore, the reflectance will be relatively low.

Figure 24A:
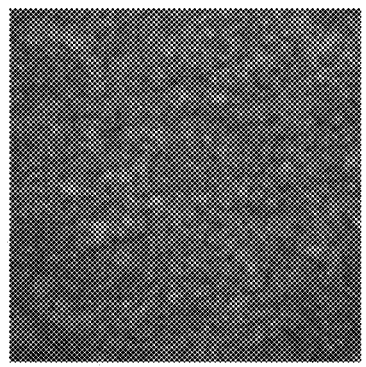
FIGS. 24A and 24B are diagrams showing examples of two-dimensional measurement results (gray scale images) in the case where light reflected from a determination image printed using MK1 ink is received by a line sensor.
Figure 24B:
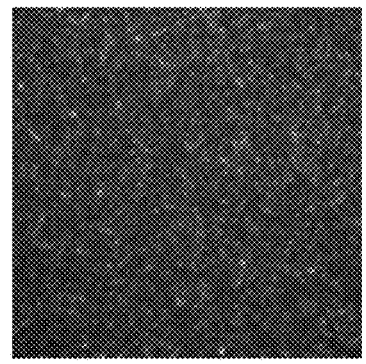

FIGS. 24A and 24B are diagrams showing examples of the two-dimensional measurement results (gray scale images) in the case where light reflected from a determination image printed by using the MK1 ink is received by the line sensor 503. FIG. 24A shows the case where the particle diameter is small and the surface asperity is small, and therefore, the amount of reflected light is large and the image is bright on the whole. FIG. 24B shows the case where the particle diameter is large and the surface asperity is large, and therefore, the amount of reflected light is small and the image is dark on the whole.

As above, as a result of the intensive research by the inventors of the present invention carried out to determine the receptive layer particle diameter on coated paper, such as matte paper, in a simple manner, the determination method based on the reflected light amount has been found out.

Figure 25:
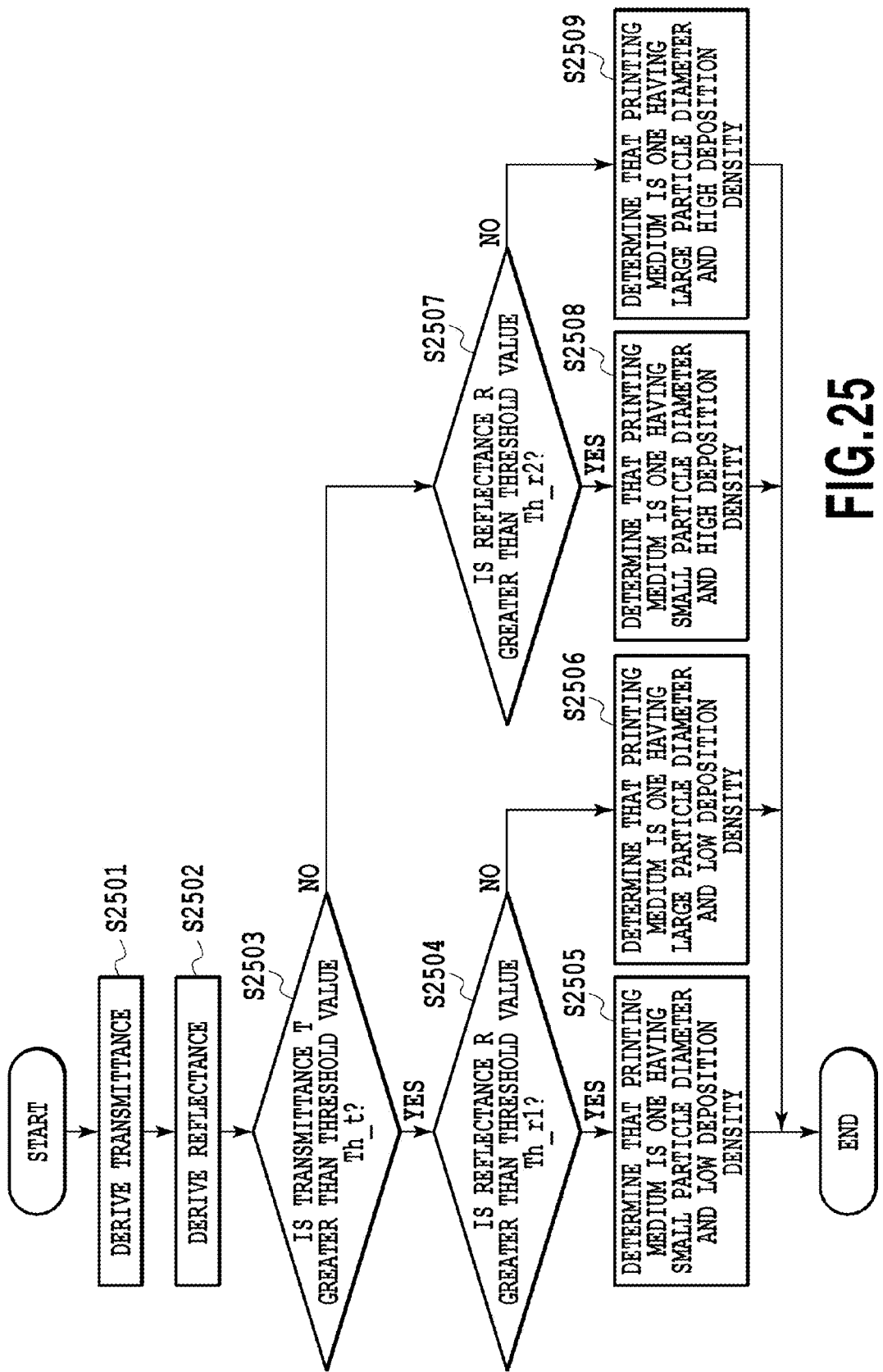
FIG. 25 is a flowchart showing a flow of specific processing in surface characteristics determination processing according to the third embodiment.

FIG. 25 is a flowchart showing a flow of the specific processing in the surface characteristics determination processing according to the present embodiment.

At step 2501, the printing medium determination apparatus 110 finds the transmittance T of the printing medium on which the determination image is printed based on the transmitted light information acquired at step 2102 described previously.

At step 2502, the printing medium determination apparatus 110 finds a reflectance R of the printing medium on which the determination image is printed based on the reflected light information acquired at step 2103 described previously. It is possible to find the reflectance R by using an expression (2) below from the two kinds of reflected light amounts (Y ref_abs and Y ref_color) included in the reflected light information.

[Mathematical expression 1]

$$\text{Reflectance } R = Y\text{ref\_color}/Y\text{ref\_abs} \quad \text{expression (2)}$$

Usually, Y ref_abs has a value of about 100 and Y ref_color has a value of about 3.3 to 2.0. In this case, the reflectance R is about 0.033 to 0.020 from the expression (2) described above.

At step 2503, the printing medium determination apparatus 110 compares the transmittance T that has been found at step 2501 and the threshold value Th_t prepared in advance and determines whether the transmittance T is greater than the threshold value Th_t. This determination processing is the same as that at step 1302 in the first embodiment and the deposition density of receptive layer particles is determined from the transmittance T. In the case where the transmittance T is greater than the threshold value Th_t according to the results of the determination, the processing proceeds to step 2504. On the other hand, in the case where the transmittance T is equal to or less than the threshold value Th_t, the processing proceeds to step 2507.

<In Case where Transmittance T is Greater than Threshold Value Th_t>

At step 2504, the printing medium determination apparatus 110 compares the reflectance R that has been found at step 2502 and a threshold value Th_r1 prepared in advance and determines whether the reflectance R is greater than the threshold value Th_r1. In this case, as the threshold value Th_r1, it may be possible to determine and hold an appropriate value in advance by preparing a plurality of kinds of recording media (samples) whose deposition density is low as shown in FIGS. 2A and 2B and by acquiring the previously-described reflected light information using these samples and deriving the reflectance. Usually, in the case where the deposition density of receptive layer particles is low and the surface asperity is small, the reflectance R is about 0.035 and in the case where the deposition density of receptive layer particles is low and the surface asperity is large, the reflectance R is about 0.026. In this case, the threshold value Th_r1 may be set to, for example, a value of 0.030. In the case where the reflectance R that has been found is greater than the threshold value Th_r1 according to the results of the determination, the processing proceeds to step 2505. On the other hand, in the case where the reflectance R that has been found is equal to or less than the threshold value Th_r1, the processing proceeds to step 2506.

At step 2505, the printing medium determination apparatus 110 determines that the printing medium is a kind of printing medium whose deposition density of receptive layer particles is low and whose receptive layer particle diameter is small (surface asperity is small) because both the transmittance T and the reflectance R are greater than the threshold values.

At step 2506, the printing medium determination apparatus 110 determines that the printing medium is a kind of printing medium whose deposition density of receptive layer particles is low and the receptive layer particle diameter is large (surface asperity is large) because the transmittance T is greater than the threshold value but the reflectance R is equal to or less than the threshold value.

<In Case where Transmittance T is Equal to or Less than Th_t>

At step 2507, the printing medium determination apparatus 110 compares the reflectance R that has been found at step 2502 and a threshold value Th_r2 prepared in advance and determines whether the reflectance R is greater than the threshold value Th_r2. In this case, as the threshold value Th_r2, it may be possible to determine and hold in advance by the same method as in the case of the previously-described threshold value Th_r1. Usually, in the case where the deposition density of receptive layer particles is high and the surface asperity is small, the reflectance R is about 0.033 and in the case where the deposition density of receptive layer particles is low and the surface asperity is large, the reflectance R is about 0.020. In this case, the threshold value Th_r2 may be set to, for example, a value of 0.025. In the case where the reflectance R that has been found is greater than the threshold value Th_r2 according to the results of the determination, the processing proceeds to step 2508. On the other hand, in the case where the reflectance R that has been found is equal to or less than the threshold value Th_r2, the processing proceeds to step 2509.

At step 2508, the printing medium determination apparatus 110 determines that the printing medium is a kind of printing medium whose deposition density of receptive layer particles is high and the receptive layer particle diameter is small (surface asperity is small) because the transmittance T is equal to or less than the threshold value and the reflectance R is greater than the threshold value.

At step 2509, the printing medium determination apparatus 110 determines that the printing medium is a kind of printing medium whose deposition density of receptive layer particles is high and the receptive layer particle diameter is large (surface asperity is large) because both the transmittance T and the reflectance R are equal to or less than the threshold values.

The results of the determination processing are input to the host 100 from the determination apparatus IF 105 as deposition density information and particle diameter information. An example of the deposition density information is the flag information as described in the first embodiment (flag "d_flg: 0" in the case where the deposition density of receptive layer particles is low, flag "d_flg: 1" in the case where the deposition density of receptive layer particles is high). An example of the particle diameter information is similar flag information (flag "r_flg: 0" in the case where the particle diameter is small, flag "r_flg: 1 in the case where the particle diameter is large). Then, the deposition density information and the particle diameter information are sent to the control unit 108 after being input to the host 100 via the determination apparatus IF 105 (see FIG. 2).

As above, by using the information on reflected light in addition to the information on transmitted light, it is possible to perform more detailed determination of the kind of printing medium.

In the present embodiment, the example is explained in which the reflectance is used as the reflected light information, but it may also be possible to derive the period of unevenness of the reflected light amount by acquiring the distribution information on reflected light and to estimate the receptive layer particle diameter from the derived period of unevenness of the reflected light amount in accordance with the second embodiment.

Further, it may also be possible to simultaneously use the reflectance and the distribution information on reflected light.

<About Printing Control Processing>

In the printing control processing at step 2105, appropriate printing processing in accordance with a purpose is performed on image data selected by a user (selected from a plurality of pieces of image data stored in the HDD 104) according to the determined kind of the printing medium.

FIG. 26 is a flowchart showing a flow of the specific processing in the printing control processing according to the present embodiment. In the present embodiment, an example is described, in which inks used in printing of image data are switched in accordance with the deposition density of receptive layer particles and the particle diameter aiming at both the improvement in density in a dark area of an image and the improvement in rubfastness.

At step 2601, the control unit 108 determines the deposition density of receptive layer particles in the printing medium that is used based on the flag (d_flg: 0 or d_flg: 1) as the deposition density information. In the case of the flag (d_flg: 0) indicating that the deposition density is low, the processing proceeds to step 2602. On the other hand, in the case of the flag (d_flg: 1) indicating that the deposition density is high, the processing proceeds to step 2607.

At step 2602, the control unit 108 determines the receptive layer particle diameter in the printing medium that is used based on the flag (r_flg: 0 or r_flg: 1) as the particle diameter information. In the case of the flag (r_flg: 0) indicating that the particle diameter is small, the processing proceeds to step 2603. On the other hand, in the case of the flag (r_flg: 1) indicating that the particle diameter is large, the processing proceeds to step 2606.

At step 2603, the control unit 108 notifies a user that the desired density cannot be achieved on the monitor 130 by displaying a message etc., and at the same time, prompts the user to input instructions whether to continue printing via, for example, a UI screen (not shown) on the monitor 130.

At step 2604, the control unit 108 determines whether the instructions to continue printing have been received from the user. In the case where the instructions to continue printing have been received, the processing proceeds to step 2605. On the other hand, in the case where the instructions to continue printing have not been received, the control unit 108 exits the present processing without performing printing.

Figure 27A:
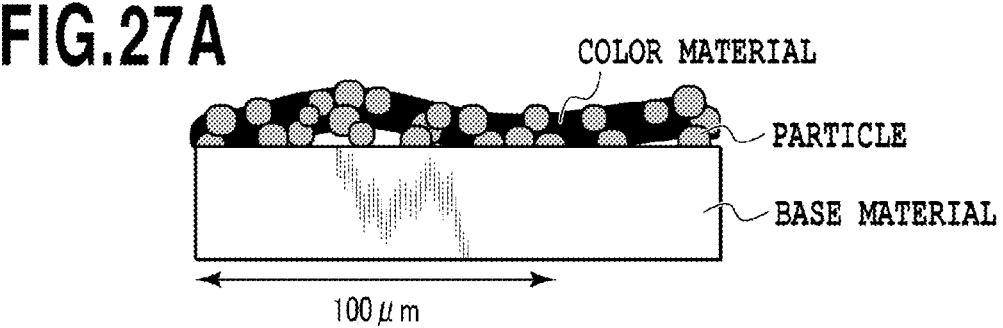
FIG. 27A shows the fixed state of ink in the case where the MK1 ink having a standard viscosity is applied to matte paper of a different type whose deposition density of receptive layer particles is low and whose particle diameter is small.

At step 2605, the control unit 108 prints the print data on the printing medium by using the MK1 ink having a relatively low viscosity (standard viscosity). The MK1 ink, which is the standard ink, is used because the coated paper of type whose deposition density of receptive layer particles is low and whose particle diameter is small is close to the plain paper and the high-quality paper and it is not possible to form an image having a high density even by using any ink. In other words, it is not necessarily required to use the MK1 ink and another ink, such as the MK2 ink and sK ink, may be used. FIG. 27A shows the fixed state of the ink in the case where the MK1 ink having a standard viscosity is applied to the matte paper of type whose deposition density of receptive layer particles is low and whose particle diameter is small. In this case, the color material easily falls into the gaps of the receptive layer, and therefore, the rubfastness is good even in the case where any ink is used.

Figure 27B:
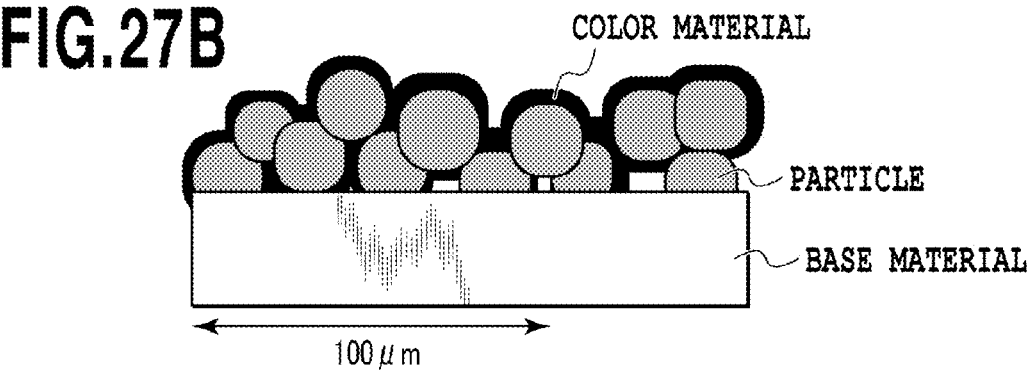
FIG. 27B shows the fixed state of the color material in the case where the MK2 ink having a relatively high viscosity is applied to the matter paper of a type whose deposition density of receptive layer is low and whose particle diameter is large.

At step 2606, the control unit 108 prints the print data on the printing medium by using the MK2 ink having a relatively high viscosity. FIG. 27B shows the fixed state of the color material in the case where the MK2 ink having a relatively high viscosity is applied to the matte paper of type whose deposition density of receptive layer particles is low and whose particle diameter is large. It is known that the color material hardly falls into the gaps of the receptive layer and there are voids, and therefore, most of the fixed positions of the color material are located on the surface of the paper. In the case of the printing medium whose receptive layer particle diameter is large, after the color material has fixed on the surface of the paper, ink peeling due to rubbing is comparatively unlikely to occur. It is known empirically that the ink having fixed on the surface with asperity is hardly peeled off, and therefore, the rubfastness is good.

At step 2607, the control unit 108 determines the receptive layer particle diameter of the printing medium that is used based on the flag (r_flg: 0 or r_flg: 1) as the particle diameter information as in the case of step 2602 described above. In the case of the flag (r_flg: 0) indicating that the particle diameter is small, the processing proceeds to step 2608. On the other hand, in the case of the flag (r_flg: 1) indicating that the particle diameter is large, the processing proceeds to step 2609.

Figure 27C:
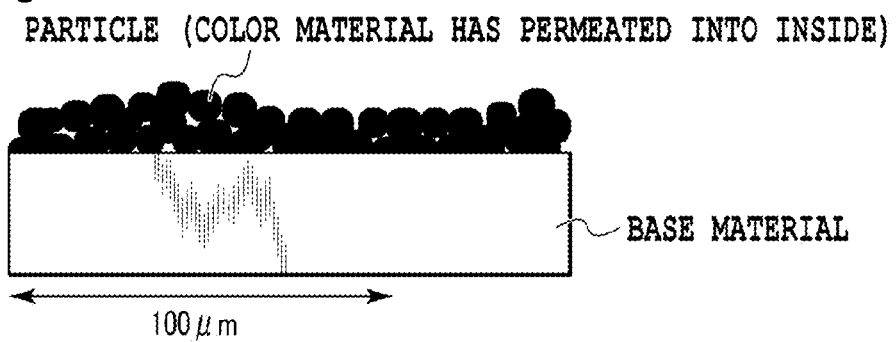
FIG. 27C shows the fixed state of the color material in the case where the dye ink (sK ink) is applied to the matter paper of a type whose deposition density of receptive layer particles is high and whose particle diameter is small.

At step 2608, the control unit 108 prints the print data on the printing medium by using the dye black sK ink. FIG. 27C shows the fixed state of the color material in the case where the dye ink (sK ink) is applied to the matte paper of type whose deposition density of receptive layer particles is high and whose particle diameter is small. The color former of the dye ink is dissolved at molecule level in the solvent, and therefore, the color material permeates into the inside of the receptive layer particle, unlike the case of the pigment ink, and the receptive layer particle itself is dyed as a result. Further, the color material permeates into the inside of the receptive layer particle, and therefore, the rubfastness is good.

Figure 27D:
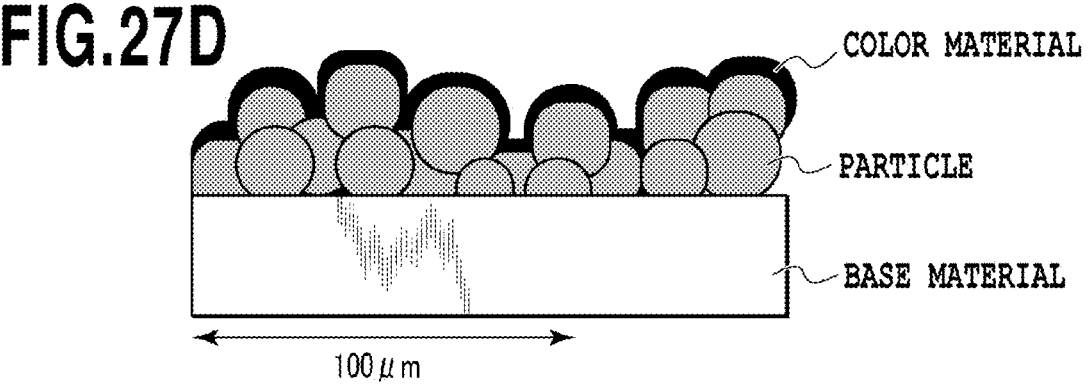
FIG. 27D shows the fixed state of the color material in the case where the MK1 ink having a standard viscosity is applied to the matte paper of a type whose deposition density of receptive layer is high and whose particle diameter is large after increasing the number of paths.

At step 2609, the control unit 108 prints the print data on the printing medium by using the MK1 ink having a standard viscosity after increasing the number of paths for multipath printing. FIG. 27D shows the fixed state of the color material in the case where the MK1 ink having a standard viscosity is applied to the matte paper of type whose deposition density of receptive layer particles is high and whose particle diameter is large after increasing the number of paths. The number of paths is increased as described above because in the case of the receptive layer whose deposition density is high, it is possible to fix the color material comparatively in the vicinity of the surface of the paper even in the case where the MK1 ink having a standard viscosity is used. However, in the case where a large amount of ink is ejected at a time, the ink easily enters the concave portions of the irregularities because the size of the surface asperity is large, and therefore, the number of paths is increased and a small amount of ink is implanted little by little. In this manner, it is possible to uniformly fix the ink comparatively in the vicinity of the surface even in the case where the size of the surface asperity is large. The ink having a viscosity higher than a standard viscosity, such as the MK2 ink, is hardly absorbed by the receptive layer, and therefore, a desired density is difficult to achieve. Because of this, in the present embodiment, the MK1 ink having a standard viscosity is used to easily achieve a desired density. As described previously, in the case where the receptive layer particle diameter is large, after the ink has fixed on the paper surface, ink peeling due to rubbing is unlikely to occur, and therefore, good rubfastness is obtained.

In the present embodiment, the case where the control to switch inks that are used is performed aiming at both the improvement in image density and the improvement in rubfastness is described. However, in the case of a printing apparatus equipped with only one kind of mat black ink, it is not possible to perform the above-described ink switching control. In this case, it may also be possible to, for example, prompt a user to determine whether to continue printing by displaying a message to the effect that a desired density cannot be achieved or a desired rubfastness cannot be maintained on the monitor 130 before performing printing processing.

In the case of a printing apparatus including an ink tank of a reactive agent to fix the ink on the paper surface, it may also be possible to perform control to change the amount of reactive agent that is used in accordance with the deposition density of receptive layer particles and the particle diameter.

Further, in the present embodiment, the printing control aiming at both the improvement in image density and the improvement in rubfastness is described, but control aiming at different purposes may be included in the category of the present invention. For example, there is a case where the feeling of matte of matte paper is lost and the matte paper has glossy characteristics, such as those of glossy paper, after printing. It is known that such a change into the glossy characteristics occurs because a large amount of color material fixes on the outermost surface of paper and the surface becomes too smooth. In the case where suppression of such a change into the glossy characteristics (maintenance of the glossy characteristics of matte paper) is aimed at, printing control to maintain the surface asperity of the matte paper by preventing an excessive amount of color material from being fixed on the outermost surface is needed. In other words, in the case where the maintenance of the glossy characteristics of the matte paper is aimed at, it is recommended to perform control so as to use an ink whose color material has a low viscosity and which easily falls into the gaps of the receptive layer instead of remaining on the outermost surface of paper, or to use the dye ink that permeates into the inside of the receptive layer particle in accordance with the deposition density of receptive layer particles and the particle diameter.

As above, according to the present embodiment, it is possible to perform more detailed determination of a printing medium by taking into consideration the deposition density of receptive layer particles and the particle diameter. Then, by performing control to switch inks that are used in printing in accordance with the determination results, both the improvement in image density and the improvement in rubfastness are achieved.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-260508, filed Dec. 17, 2013, which is hereby incorporated by reference wherein in its entirety.

What is claimed is:

1. An information processing apparatus for determining a printing medium having a receptive layer, comprising:

a transmitted light information acquisition unit configured to acquire information on transmitted light by irradiating a printing medium on which a determination image is printed with light;

a surface characteristics determination unit configured to determine the surface characteristics of a printing medium on which the determination image is printed based on the information on transmitted light; and a control unit configured to perform control of printing so as to switch a color material that is used in accordance with the determination results of the surface characteristics of the printing medium determined by the surface characteristics determination unit, wherein the control unit controls so as to print by using a color material having a higher viscosity in a case where a deposition density of particles constituting the receptive layer is lower.

2. The information processing apparatus according to claim 1, wherein the information on transmitted light is information on an amount of light having passed through a region in which the determination image is printed and on an amount of light having passed through a region in which the determination image is not printed, both regions being on the printing medium on which the determination image is printed.

3. The information processing apparatus according to claim 2, wherein the surface characteristics determination unit finds a transmittance of the printing medium on which the determination image is printed from the information on transmitted light and determines a deposition density of particles constituting the receptive layer from the transmittance that has been found.

4. The information processing apparatus according to claim 1, wherein the information on transmitted light is distribution information on light having passed through the region in which the determination image is printed of the printing medium on which the determination image is printed.

5. The information processing apparatus according to claim 4, wherein the surface characteristics determination unit finds a period of unevenness of a deposition density of particles constituting a receptive layer of a printing medium on which the determination image is printed from the information on transmitted light and determines the deposition density of particles constituting the receptive layer from the period of unevenness that has been found.

6. The information processing apparatus according to claim 1, further comprising a reflected light information acquisition unit configured to acquire information on reflected light by irradiating a printing medium on which the determination image is printed with light, wherein the surface characteristics determination unit determines the surface characteristics of the printing medium on which the determination image is printed based on the information on transmitted light and the information on reflected light.

7. The information processing apparatus according to claim 6, wherein the information on reflected light includes information on an amount of light having been reflected from a region in which the determination image is printed, and information on an amount of reflected light obtained by irradiating a reference plate with light.

8. The information processing apparatus according to claim 7, wherein the surface characteristics determination unit derives a reflectance of a printing medium on which the determination image is printed from the information on reflected light and determines the particle diameter of particles constituting the receptive layer from the derived reflectance.

9. The information processing apparatus according to claim 1, wherein a particle diameter of particles constituting the receptive layer of the printing medium is 3 μm or more.

10. The information processing apparatus according to claim 1, further comprising a determination image printing unit configured to form a determination image on a printing medium by using color material,
wherein the color material is a pigment ink.

11. An information processing method of an information processing apparatus for determining a printing medium having a receptive layer, the method comprising the steps of:
acquiring, by a transmitted light information acquisition unit, information on transmitted light by irradiating a printing medium on which a determination image is printed with light;
determining the surface characteristics of the printing medium on which the determination image is printed based the information on transmitted light; and
controlling printing so as to switch a color material that is used in accordance with the determination results of the surface characteristics of the printing medium determined in the determining step,
wherein the controlling is performed so as to print by using a color material having a higher viscosity in a case where a deposition density of particles constituting the receptive layer is lower.

12. A non-transitory computer readable storage medium storing a program for causing a computer to function as an information processing apparatus for determining a printing medium having a receptive layer, the program comprising computer executable code to perform the steps of:
acquiring, by a transmitted light information acquisition unit, information on transmitted light by irradiating a printing medium on which a determination image is printed with light;
determining the surface characteristics of the printing medium on which the determination image is printed based on the information on transmitted light; and
controlling printing so as to switch a color material that is used in accordance with the determination results of the surface characteristics of the printing medium determined in the determining step,
wherein the controlling is performed so as to print by using a color material having a higher viscosity in a case where a deposition density of particles constituting the receptive layer is lower.

13. An information processing apparatus for determining a printing medium having a receptive layer, comprising:
a transmitted light information acquisition unit configured to acquire information on transmitted light by irradiating a printing medium on which a determination image is printed with light;
a surface characteristics determination unit configured to determine the surface characteristics of a printing medium on which the determination image is printed based on the information on transmitted light; and
a control unit configured to perform control of printing so as to switch a color material that is used in accordance with the determination results of the surface characteristics of the printing medium determined by the surface characteristics determination unit,
wherein the control unit controls so as to print by using a color material having a higher viscosity in a case where a particle diameter of particles constituting the receptive layer is larger.

14. An information processing method of an information processing apparatus for determining a printing medium having a receptive layer, the method comprising the steps of:
acquiring, by a transmitted light information acquisition unit, information on transmitted light by irradiating a printing medium on which a determination image is printed with light;
determining the surface characteristics of the printing medium on which the determination image is printed based the information on transmitted light; and
controlling printing so as to switch a color material that is used in accordance with the determination results of the surface characteristics of the printing medium determined in the determining step,
wherein the controlling is performed so as to print by using a color material having a higher viscosity in a case where a particle diameter of particles constituting the receptive layer is larger.

15. A non-transitory computer readable storage medium storing a program for causing a computer to function as an information processing apparatus for determining a printing medium having a receptive layer, the program comprising computer executable code to perform the steps of:
acquiring, by a transmitted light information acquisition unit, information on transmitted light by irradiating a printing medium on which a determination image is printed with light;
determining the surface characteristics of the printing medium on which the determination image is printed based the information on transmitted light; and
controlling printing so as to switch a color material that is used in accordance with the determination results of the surface characteristics of the printing medium determined in the determining step,
wherein the controlling is performed so as to print by using a color material having a higher viscosity in a case where a particle diameter of particles constituting the receptive layer is larger.

* * * * *